(12) United States Patent
Behnam et al.

(10) Patent No.: US 8,758,792 B2
(45) Date of Patent: Jun. 24, 2014

(54) BONE MATRIX COMPOSITIONS AND METHODS

(71) Applicant: Warsaw Orthopedic, Inc., Warsaw, IN (US)

(72) Inventors: Keyvan Behnam, Red Bank, NJ (US); Guobao Wei, Milltown, NJ (US); Nanette Forsyth, Bayville, NJ (US)

(73) Assignee: Warsaw Orthopedic, Inc., Warsaw, IN (US)

(*) Notice: Subject to any disclaimer, the term of this patent is extended or adjusted under 35 U.S.C. 154(b) by 0 days.

(21) Appl. No.: 13/746,516

(22) Filed: Jan. 22, 2013

(65) Prior Publication Data

US 2013/0136777 A1 May 30, 2013

Related U.S. Application Data

(63) Continuation of application No. 12/140,044, filed on Jun. 16, 2008, now Pat. No. 8,357,384.

(60) Provisional application No. 60/957,614, filed on Aug. 23, 2007, provisional application No. 60/948,979, filed on Jul. 10, 2007, provisional application No. 60/944,411, filed on Jun. 15, 2007.

(51) Int. Cl.
*A61K 35/00* (2006.01)
*A61K 35/32* (2006.01)

(52) U.S. Cl.
USPC ........... 424/422; 424/549; 427/2.26; 606/909

(58) Field of Classification Search
None
See application file for complete search history.

(56) References Cited

U.S. PATENT DOCUMENTS

| | | | |
|---|---|---|---|
| 6,294,041 B1 * | 9/2001 | Boyce et al. | 156/275.5 |
| 6,294,187 B1 * | 9/2001 | Boyce et al. | 424/422 |
| 6,723,131 B2 * | 4/2004 | Muschler | 623/23.51 |
| 2005/0025667 A1 * | 2/2005 | Christensen et al. | 422/33 |

FOREIGN PATENT DOCUMENTS

WO    WO 2005/084578 A1 *    9/2005

* cited by examiner

*Primary Examiner* — Elizabeth C Kemmerer
(74) *Attorney, Agent, or Firm* — Sorell Lenna & Schmidt LLP

(57) ABSTRACT

Osteoinductive compositions and implants having increased biological activities, and methods for their production, are provided. The biological activities that may be increased include, but are not limited to, bone forming; bone healing; osteoinductive activity, osteogenic activity, chondrogenic activity, wound healing activity, neurogenic activity, contraction-inducing activity, mitosis-inducing activity, differentiation-inducing activity, chemotactic activity, angiogenic or vasculogenic activity, and exocytosis or endocytosis-inducing activity. In one embodiment, a method for producing an osteoinductive composition comprises providing partially demineralized bone, treating the partially demineralized bone to disrupt the collagen structure of the bone, and optionally providing a tissue-derived extract and adding the tissue-derived extract to the partially demineralized bone. In another embodiment, an implantable osteoinductive and osteoconductive composition comprises partially demineralized bone, wherein the collagen structure of the bone has been disrupted, and, optionally, a tissue-derived extract.

16 Claims, 5 Drawing Sheets

13 Week Results

Autograft

Surface Demin
Heat Treated
Particles

BONE MATRIX COMPOSITIONS AND METHODS

CROSS-REFERENCE TO RELATED APPLICATION(S)

This application is a continuation application of U.S. application Ser. No. 12/140,044, now U.S. Pat. No. 8,357,384, filed on Jun. 16, 2008, which claims the benefit of U.S. Patent Application Ser. No. 60/944,411 filed Jun. 15, 2007; U.S. Patent Application Ser. No. 60/948,979 filed Jul. 10, 2007; and U.S. Patent Application Ser. No. 60/957,614 filed Aug. 23, 2007, the contents of all the aforementioned applications are incorporated by reference herein.

BACKGROUND

Introduction

Mammalian bone tissue is known to contain one or more proteinaceous materials, presumably active during growth and natural bone healing, that can induce a developmental cascade of cellular events resulting in endochondral bone formation. The active factors have variously been referred to in the literature as bone morphogenetic or morphogenic proteins (BMPs), bone inductive proteins, bone growth or growth factors, osteogenic proteins, or osteoinductive proteins. These active factors are collectively referred to herein as osteoinductive factors.

It is well known that bone contains these osteoinductive factors. These osteoinductive factors are present within the compound structure of cortical bone and are present at very low concentrations, e.g., 0.003%. Osteoinductive factors direct the differentiation of pluripotential mesenchymal cells into osteoprogenitor cells that form osteoblasts. Based upon the work of Marshall Urist as shown in U.S. Pat. No. 4,294,753, issued Oct. 13, 1981, proper demineralization of cortical bone exposes the osteoinductive factors, rendering it osteoinductive, as discussed more fully below.

Overview of Bone Grafts

The rapid and effective repair of bone defects caused by injury, disease, wounds, or surgery is a goal of orthopaedic surgery. Toward this end, a number of compositions and materials have been used or proposed for use in the repair of bone defects. The biological, physical, and mechanical properties of the compositions and materials are among the major factors influencing their suitability and performance in various orthopaedic applications.

Autologous cancellous bone ("ACB"), also known as autograft or autogenous bone, long has been considered the gold standard for bone grafts. ACB is osteoinductive and nonimmunogenic, and, by definition, has all of the appropriate structural and functional characteristics appropriate for the particular recipient. Unfortunately, ACB is only available in a limited number of circumstances. Some individuals lack ACB of appropriate dimensions and quality for transplantation, and donor site pain and morbidity can pose serious problems for patients and their physicians.

Bone grafting applications are differentiated by the requirements of the skeletal site. Certain applications require a "structural graft" in which one role of the graft is to provide mechanical or structural support to the site. Such grafts contain a substantial portion of mineralized bone tissue to provide the strength needed for load-bearing. Examples of applications requiring a "structural graft" include intercalary grafts, spinal fusion, joint plateaus, joint fusions, large bone reconstructions, etc. Other applications require an "osteogenic graft" in which one role of the graft is to enhance or accelerate the growth of new bone tissue at the site. Such grafts contain a substantial portion of demineralized bone tissue to improve the osteoinductivity needed for growth of new bone tissue. Examples of applications requiring "osteogenic graft" include deficit filling, spinal fusions, joint fusions, etc. Grafts may also have other beneficial biological properties, such as, for example, serving as delivery vehicles for bioactive substances. Bioactive substances include physiologically or pharmacologically active substances that act locally or systemically in the host.

When mineralized bone is used in osteoimplants, it is primarily because of its inherent strength, i.e., its load-bearing ability at the recipient site. The biomechanical properties of osteoimplants upon implantation are determined by many factors, including the specific site from which the bone used to make the osteoimplant is taken; various physical characteristics of the donor tissue; and the method chosen to prepare, preserve, and store the bone prior to implantation, as well as the type of loading to which the graft is subjected.

Structural osteoimplants are conventionally made by processing, and then machining or otherwise shaping cortical bones collected for transplant purposes. Osteoimplants may comprise monolithic bone of an aggregate of particles. Further, osteoimplants may be substantially solid, flowable, or moldable. Cortical bone can be configured into a wide variety of configurations depending on the particular application for the structural osteoimplant. Structural osteoimplants are often provided with intricate geometries, e.g., series of steps; concave or convex surfaces; tapered surfaces; flat surfaces; surfaces for engaging corresponding surfaces of adjacent bone, tools, or implants, hex shaped recesses, threaded holes; serrations, etc.

One problem associated with many monolithic structural osteoimplants, particularly those comprising cortical bone, is that they are never fully incorporated by remodeling and replacement with host tissue. Since repair is a cellular-mediated process, dead (non-cellular, allograft or xenograft) bone is unable to repair itself. When the graft is penetrated by host cells and host tissue is formed, the graft is then capable of repair. It has been observed that fatigue damage is usually the result of a buildup of unrepaired damage in the tissue. Therefore, to the extent that the implant is incorporated and replaced by living host bone tissue, the body can then recognize and repair damage, thus eliminating failure by fatigue. In applications where the mechanical load-bearing requirements of the osteoimplant are challenging, e.g., intervertebral spinal implants for spinal fusion, lack of substantially complete replacement by host bone tissue may compromise the osteoimplant by subjecting it to repeated loading and cumulative unrepaired damage in the tissue (mechanical fatigue) within the implant material. Thus, it is desirable that the osteoimplant has the capacity to support load initially and be capable of gradually transferring this load to the host bone tissue as it remodels the implant.

Much effort has been invested in the identification and development of alternative bone graft materials. Urist published seminal articles on the theory of bone induction and a method for decalcifying bone, i.e., making demineralized bone matrix (DBM). Urist M. R., Bone Formation by Autoinduction, Science 1965; 150(698):893-9; Urist M. R. et al., The Bone Induction Principle, Clin. Orthop. Rel. Res. 53:243-283, 1967. DBM is an osteoinductive material in that it induces bone growth when implanted in an ectopic site of a rodent, owing to the osteoinductive factors contained within the DBM. It is now known that there are numerous osteoinductive factors, e.g., BMP2, BMP4, BMP6, BMP7, which are part of the transforming growth factor-beta (TGF-beta) superfamily. BMP-2 has become the most important and widely studied of the BMP family of proteins. There are also other proteins present in DBM that are not osteoinductive alone but still contribute to bone growth, including fibroblast growth factor-2 (FGF-2), insulin-like growth factor-I and -II (IGF-I and IGF-II), platelet derived growth factor (PDGF), and transforming growth factor-beta 1 (TGF-beta.1).

Accordingly, a known technique for promoting the process of incorporation of osteoimplants is demineralization of portions of, or the entire volume of, the implant. The process of demineralizing bone grafts is well known. In this regard see, Lewandrowski et al., J. Biomed Materials Res, 31, pp. 365 372 (1996); Lewandrowski et al., Calcified Tiss. Int., 61, pp. 294 297 (1997); Lewandrowski et al., J. Ortho. Res., 15, pp. 748 756 (1997), the contents of each of which is incorporated herein by reference.

DBM implants have been reported to be particularly useful (see, for example, U.S. Pat. Nos. 4,394,370, 4,440,750, 4,485, 097, 4,678,470, and 4,743,259; Mulliken et al., *Calcif Tissue Int.* 33:71, 1981; Neigel et al., *Opthal. Plast. Reconstr. Surg.* 12:108, 1996; Whiteman et al., *J. Hand. Surg.* 18B:487, 1993; Xiaobo et al., *Clin. Orthop.* 293:360, 1993, each of which is incorporated herein by reference). DBM typically is derived from cadavers. The bone is removed aseptically and treated to kill any infectious agents. The bone is particulated by milling or grinding, and then the mineral component is extracted by various methods, such as by soaking the bone in an acidic solution. The remaining matrix is malleable and can be further processed and/or formed and shaped for implantation into a particular site in the recipient. The demineralized bone particles or fibers can be formulated with biocompatible excipients to enhance surgical handling properties and conformability to the defect or surgery site. Demineralized bone prepared in this manner contains a variety of components including proteins, glycoproteins, growth factors, and proteoglycans. Following implantation, the presence of DBM induces cellular recruitment to the site of injury. The recruited cells may eventually differentiate into bone forming cells. Such recruitment of cells leads to an increase in the rate of wound healing and, therefore, to faster recovery for the patient.

Demineralization provides the osteoimplant, whether monolithic, aggregate, flowable, or moldable, with a degree of flexibility. However, removal of the mineral components of bone significantly reduces mechanical strength of bone tissue. See, Lewandrowski et al., Clinical Ortho. Rel. Res., 317, pp. 254 262 (1995). Thus, demineralization sacrifices some of the load-bearing capacity of cortical bone and as such may not be suitable for all osteoimplant designs.

While the collagen-based matrix of DBM is relatively stable, the osteoinductive factors within the DBM matrix are rapidly degraded. The osteogenic activity of the DBM may be significantly degraded within 24 hours after implantation, and in some instances the osteogenic activity may be inactivated within 6 hours. Therefore, the osteoinductive factors associated with the DBM are only available to recruit cells to the site of injury for a short time after transplantation. For much of the healing process, which may take weeks to months, the implanted material may provide little or no assistance in recruiting cells. Further, most DBM formulations are not load-bearing.

Extracting Proteins

The potential utility of osteoinductive factors has been recognized widely. It has been contemplated that the availability of osteoinductive factors could revolutionize orthopedic medicine and certain types of plastic surgery, dental, and various periodontal and craniofacial reconstructive procedures.

Urist's U.S. Pat. No. 4,294,753, herein incorporated by reference, was the first of many patents on a process for extracting BMP from DBM. At the time of the Urist '753 patent, BMP was referred to generally. It is now known that there are multiple forms of BMP. The Urist process became widely adopted, and though different users may use different chemical agents from those disclosed in the basic Urist process, the basic layout of the steps of the process remains widely used today as one of the main methods of extracting BMP from DBM. See, e.g., U.S. Pub 2003/0065392 (2003); U.S. Pub 2002/0197297 (2002). Urist reported that his basic process actually results in generally low yields of BMP per unit weight of DBM.

Implanting Extracted Proteins

Successful implantation of the osteoinductive factors for endochondral bone formation requires association of the proteins with a suitable carrier material capable of maintaining the proteins at an in vivo site of application. The carrier generally is biocompatible, in vivo biodegradable, and sufficiently porous to allow cell infiltration. Insoluble collagen particles that remain after guanidine extraction and delipidation of pulverized bone generally have been found effective in allogenic implants in some species. However, studies have shown that while osteoinductive proteins are useful cross species, the collagenous bone matrix generally used for inducing endochondral bone formation is species-specific. Sampath and Reddi, (1983) Proc. Nat. Acad. Sci. USA 80: 6591-6594.

European Patent Application Serial No. 309,241, published Mar. 29, 1989, herein incorporated by reference, discloses a device for inducing endochondral bone formation comprising an osteogenic protein preparation, and a matrix carrier comprising 60-98% of either mineral component or bone collagen powder and 2-40% atelopeptide hypoimmunogenic collagen.

The use of pulverized exogenous bone growth material, e.g., derived from demineralized allogenic or xenogenic bone, in the surgical repair or reconstruction of defective or diseased bone in human or other mammalian/vertebrate species is known. See, in this regard, the disclosures of U.S. Pat. Nos. 4,394,370, 4,440,750, 4,472,840, 4,485,097, 4,678,470, 4,743,259, 5,284,655, 5,290,558; Bolander et al., "The Use of Demineralized Bone Matrix in the Repair of Segmental Defects," The Journal of Bone and Joint Surgery, Vol. 68-A, No. 8, pp. 1264-1273; Glowacki et al, "Demineralized Bone Implants," Symposium on Horizons in Plastic Surgery, Vol. 12, No. 2; pp. 233-241 (1985); Gepstein et al., "Bridging Large Defects in Bone by Demineralized Bone Matrix in the Form of a Powder," The Journal of Bone and Joint Surgery, Vol. 69-A, No. 7, pp. 984-991 (1987); Mellonig, "Decalcified Freeze-Dried Bone Allograft as an Implant Material In Human Periodontal Defects," The International Journal of Periodontics and Restorative Dentistry, pp. 41-45 (June 1984); Kaban et al., "Treatment of Jaw Defects with Demineralized Bone Implants," Journal of Oral and Maxillofacial Surgery, pp. 623-626 (Jun. 6, 1989); and Todescan et al., "A Small Animal Model for Investigating Endosseous Dental Implants: Effect of Graft Materials on Healing of Endosseous, Porous-Surfaced Implants Placed in a Fresh Extraction Socket," The International Journal of Oral & Maxillofacial Implants Vol. 2, No. 4, pp. 217-223 (1987), all herein incorporated by reference.

A variety of approaches have been explored in an attempt to recruit progenitor cells or chondrocytes into an osteochondral or chondral defect. For example, penetration of subchondral bone has been performed in order to access mesenchymal stem cells (MSCs) in the bone marrow, which have the potential to differentiate into cartilage and bone. Steadman, et al., "Microfracture: Surgical Technique and Rehabilitation to Treat Chondral Defects," *Clin. Orthop.*, 391 S:362-369 (2001). In addition, some factors in the body are believed to aid in the repair of cartilage. For example, transforming growth factors beta (TGF-β) have the capacity to recruit progenitor cells into a chondral defect from the synovium or elsewhere when loaded in the defect. Hunziker, et al., "Repair of Partial Thickness Defects in Articular Cartilage: Cell Recruitment From the Synovial Membrane," *J Bone Joint Surg.*, 78-A:721-733 (1996). However, the application of growth factors to bone and cartilage implants has not resulted in the expected increase in osteoinductive or chondrogenic activity.

U.S. Pat. No. 7,132,110, herein incorporated by reference, describes an osteogenic composition prepared by a process including the steps of subjecting demineralized bone to an extraction medium to produce an insoluble extraction product and a soluble extraction product, separating the insoluble extraction product and the soluble extraction product, drying the soluble extraction product to remove all or substantially all of the moisture in the soluble extraction product, and combining the dried soluble extraction product with demineralized bone particles. Studies using the process have shown that the formed osteogenic composition does not have appreciably increased osteoinductive properties when compared to the demineralized bone particles to which the dried soluble extraction product is added. It was further determined that the demineralized bone from which the extraction products are extracted does not exhibit appreciably decreased osteoinductive properties when compared with its properties prior to extraction. It is thus theorized that the extraction process withdraws only a small fraction of available tissue repair factors.

Overall, current bone and cartilage graft formulations have various drawbacks. The osteoinductive factors within the matrices can be rapidly degraded and, thus, factors associated with the matrix are only available to recruit cells to the site of injury for a short time after implantation. Further, in certain instances the current graft formulations exhibit limited capacity to stimulate tissue formation.

BRIEF SUMMARY

Osteoinductive compositions and implants having increased biological activities, and methods for their production, are provided. The biological activities that may be increased include, but are not limited to, bone forming, bone healing, osteoinductive activity, osteogenic activity, chondrogenic activity, wound healing activity, neurogenic activity, contraction-inducing activity, mitosisinducing activity, differentiation-inducing activity, chemotactic activity, angiogenic or vasculogenic activity, and exocytosis or endocytosis-inducing activity.

In one embodiment, a method for producing an osteoinductive composition is provided. The method comprises providing partially demineralized bone, treating the partially demineralized bone to disrupt the collagen structure of the bone, providing a tissue-derived extract, and adding the tissue-derived extract to the partially demineralized bone.

In another embodiment, an implantable osteoinductive and osteoconductive composition is provided. The composition comprises partially demineralized bone, wherein the collagen structure of the bone has been disrupted, and a tissue-derived extract.

In yet another embodiment, a method for producing an osteoinductive composition is provided. The method comprises providing surface demineralized bone and treating the surface demineralized bone to disrupt the collagen structure of the bone.

In a further embodiment, an implantable osteoinductive and osteoconductive composition is provided. The composition comprises surface demineralized bone or substantially fully demineralized, wherein the collagen structure of the bone has been disrupted.

In yet a further embodiment, a method for treating a bone condition is provided. The method comprises providing partially demineralized bone, treating the partially demineralized bone to disrupt the collagen structure of the bone, providing a tissue-derived extract, adding the tissue-derived extract to the partially demineralized bone, and implanting the tissue-derived extract and partially demineralized bone.

In another embodiment, an osteoinductive composition is provided comprising surface demineralized bone particles, the bone particles ranging from approximately 1 mm to approximately 4 mm in length, wherein the collagen structure of the bone has been disrupted. The osteoinductive composition further comprises demineralized bone matrix and tissue derived extract.

This application refers to various patents, patent applications, journal articles, and other publications, all of which are incorporated herein by reference. The following documents are incorporated herein by reference: PCT/US04/43999; PCT/US05/003092; US 2003/0143258 A1; PCT/US02/32941; *Current Protocols in Molecular Biology, Current Protocols in Immunology, Current Protocols in Protein Science, and Current Protocols in Cell Biology*, John Wiley & Sons, N.Y., edition as of July 2002; Sambrook, Russell, and Sambrook, *Molecular Cloning: A Laboratory Manual*, 3rd ed., Cold Spring Harbor Laboratory Press, Cold Spring Harbor, 2001; Rodd 1989 "Chemistry of Carbon Compounds," vols. 1-5 and supps, Elsevier Science Publishers, 1989; "Organic Reactions," vols 1-40, John Wiley and Sons, New York, N.Y., 1991; March 2001, "Advanced Organic Chemistry," 5th ed. John Wiley and Sons, New York, N.Y. In the event of a conflict between the specification and any of the incorporated references, the specification shall control. Where numerical values herein are expressed as a range, endpoints are included.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

DEFINITIONS

Figure 1:
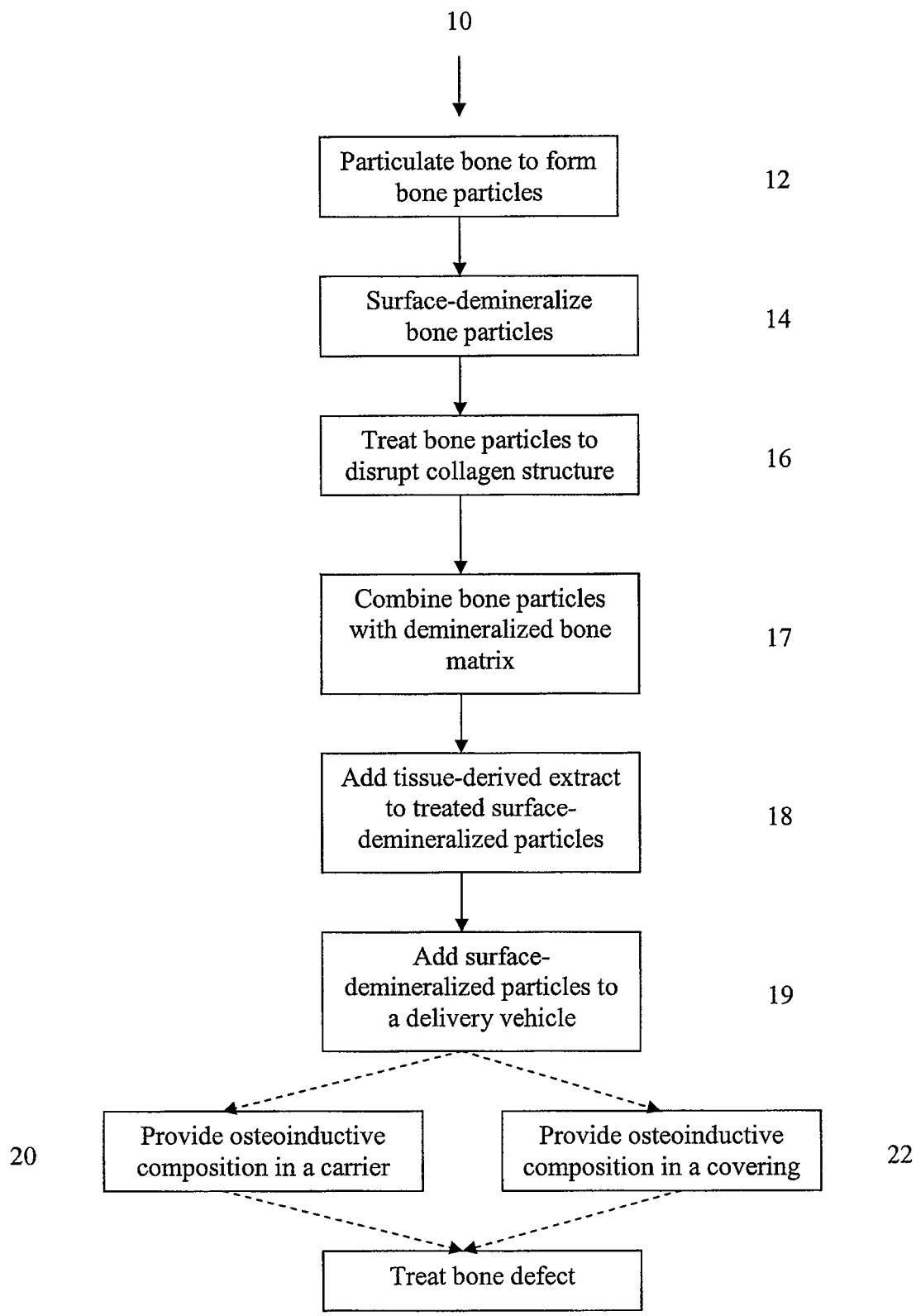
FIG. 1 illustrates a flowchart of a method for producing an osteoinductive composition in accordance with one embodiment.

Bioactive Agent or Bioactive Compound, as used herein, to refers to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. In some embodiments, the bioactive agent is a growth factor, cytokine, extracellular matrix molecule or a fragment or derivative thereof, for example, a cell attachment sequence such as RGD. A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996; and the United States Pharmacopeia-25/National Formulary-20, published by the United States Pharmacopeial Convention, Inc., Rockville Md., 2001, each of which is incorporated herein by reference.

Biocompatible, as used herein, refers to materials that, upon administration in vivo, do not induce undesirable long-term effects.

Bone, as used herein, refers to bone that is cortical, cancellous or cortico-cancellous of autogenous, allogenic, xenogenic, or transgenic origin.

Bone Fibers, as used herein, refer to elongate bone particles comprising threads or filaments having a median length to median thickness ratio of at least about 10:1 and up to about 500:1, a median length of from about 2 mm to about 400 mm, a medium width of about 2 mm to about 5 mm, and a median thickness of from about 0.02 mm to about 2 mm.

Bone Particle, as used herein, refers to a piece of particulated bone with wide range of average particle size ranging from relatively fine powders to coarse grains and even larger chips. For example, the bone particles may range in average particle size from about 0.1 mm to about 15 mm in its largest dimension, or from about 0.5 to about 1.0 mm. The bone particles may be generally round and have a radius, may be elongated, may be irregular, or may be in any other suitable configuration. The bone particles can be obtained from about cortical, cancellous and/or corticocancellous autogenous, allogeneic, xenogeneic, or transgenic bone tissue.

Demineralized, as used herein, refers to any material generated by removing mineral material from tissue, e.g., bone tissue. In certain embodiments, the demineralized compositions described herein include preparations containing less than 5% calcium. In some embodiments, the demineralized compositions may comprise less than 1% calcium by weight. Partially demineralized bone is intended to refer to preparations with greater than 5% calcium by weight but containing less than 100% of the original starting amount of calcium. In some embodiments, demineralized bone has less than 95% of its original mineral content. Percentage of demineralization may refer to percentage demineralized by weight, or to percentage demineralized by depth, as described with reference to FIGS. 4a and 4b. "Demineralized" is intended to encompass such expressions as "substantially demineralized," "partially demineralized," "surface demineralized," and "fully demineralized." "Partially demineralized" is intended to encompass "surface demineralized."

Demineralized bone matrix (DBM), as used herein, refers to any material generated by removing mineral material from bone tissue. In some embodiments, the DBM compositions as used herein include preparations containing less than 5% calcium and preferably less than 1% calcium by weight. In other embodiments, the DBM compositions comprise partially demineralized bone (e.g., preparations with greater than 5% calcium by weight but containing less than 100% of the original starting amount of calcium).

Osteoconductive, as used herein, refers to the ability of a non-osteoinductive substance to serve as a suitable template or substance along which bone may grow.

Osteogenic, as used herein, refers to materials containing living cells capable of differentiation into bone tissue.

Osteoimplant as used herein refers to any bone-derived implant prepared in accordance with the embodiments of this invention and therefore is intended to include expressions such as bone membrane, bone graft, etc.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," *Clinical Orthopaedics & Rel. Res.,* 357:219-228, December 1998, incorporated herein by reference. In other instances, osteoinduction is considered to occur through cellular recruitment and induction of the recruited cells to an osteogenic phenotype. Osteoinductivity score refers to a score ranging from 0 to 4 as determined according to the method of Edwards et al. (1998) or an equivalent calibrated test. In the method of Edwards et al., a score of "0" represents no new bone formation; "1" represents 1%-25% of implant involved in new bone formation; "2" represents 26-50% of implant involved in new bone formation; "3" represents 51%-75% of implant involved in new bone formation; and "4" represents >75% of implant involved in new bone formation. In most instances, the score is assessed 28 days after implantation. However, the osteoinductivity score may be obtained at earlier time points such as 7, 14, or 21 days following implantation. In these instances it may be desirable to include a normal DBM control such as DBM powder without a carrier, and if possible, a positive control such as BMP. Occasionally osteoinductivity may also be scored at later timepoints such as 40, 60, or even 100 days following implantation. Percentage of osteoinductivity refers to an osteoinductivity score at a given time point expressed as a percentage of activity, of a specified reference score. Osteoinductivity may be assessed in an athymic rat or in a human. Generally, as discussed herein, an osteoinductive score is assessed based on osteoinductivity in an athymic rat.

Pressed bone fibers, as used herein, refer to bone fibers formed by applying pressure to bone stock. The bone utilized as the starting, or stock, material may range in size from relatively small pieces of bone to bone of such dimensions as to be recognizable as to its anatomical origin. The bone may be substantially fully demineralized, surface demineralized, partially demineralized, or nondemineralized. In general, the pieces or sections of whole bone stock can range from about 1 to about 400 mm, from about 5 to about 100 mm, in median length, from about 0.5 to about 20 mm, or from about 2 to about 10 mm, in median thickness and from about 1 to about 20 mm, or from about 2 to about 10 mm, in median width. Forming bone fibers by pressing results in intact bone fibers of longer length than other methods of producing elongate bone fibers, with the bone fibers retaining more of the native collagen structure. The bone may be particulated via pressure applied to the bone, as discussed in U.S. Pat. No. 7,323,193, herein incorporated by reference.

Proteases, as used herein, refers to protein-cleaving enzymes that cleave peptide bonds that link amino acids in protein molecules to generate peptides and protein fragments. A large collection of proteases and protease families has been identified. Some exemplary proteases include serine proteases, aspartyl proteases, acid proteases, alkaline proteases, metalloproteases, carboxypeptidase, aminopeptidase, cysteine protease, collagenase, etc. An exemplary family of proteases is the proprotein convertase family, which includes furin. Dubois et al., *American Journal of Pathology* (2001) 158(1):305316. Members of the proprotein convertase family of proteases are known to proteolytically process proTGFs and proBMPs to their active mature forms. Dubois et al., *American Journal of Pathology* (2001) 158(1):305-316; Cui et al., *The Embo Journal* (1998) 17(16):4735-4743; Cui et al., *Genes & Development* (2001) 15:2797-2802, each incorporated by reference herein.

Protease inhibitors, as used herein, refers to chemical compounds capable of inhibiting the enzymatic activity of protein cleaving enzymes (i.e., proteases). The proteases inhibited by these compounds include serine proteases, acid proteases, metalloproteases, carboxypeptidase, aminopeptidase, cysteine protease, etc. The protease inhibitor may act specifically to inhibit only a specific protease or class of proteases, or it may act more generally by inhibiting most if not all proteases. Preferred protease inhibitors are protein or peptide based and are commercially available from chemical companies such as Aldrich-Sigma. Protein or peptide-based inhibitors which adhere to the DBM (or calcium phosphate or ceramic carrier) may be preferred because they remain associated with the matrix providing a stabilizing effect for a longer period of time than freely diffusible inhibitors. Examples of protease inhibitors include aprotinin, 4-(2-aminoethyl) benzenesulfonyl fluoride (AEBSF), amastatin-HCl, alpha1-antichymotrypsin, antithrombin III, alpha1-antitrypsin, 4-aminophenylmethane sulfonyl-fluoride (APMSF), arphamenine A, arphamenine B, E-64, bestatin, CA-074, CA-074-Me, calpain inhibitor I, calpain inhibitor II, cathepsin inhibitor, chymostatin, diisopropylfluorophosphate (DFP), dipeptidylpeptidase IV inhibitor, diprotin A, E-64c, E-64d, E-64, ebelactone A, ebelactone B, EGTA, elastatinal, foroxymithine, hirudin, leuhistin, leupeptin, alpha2macroglobulin, phenylmethylsulfonyl fluo4de (PMSF), pepstatin A, phebestin, 1,10phenanthroline, phosphoramidon, chymostatin, benzamidine HCl, antipain, epsilon aminocaproic acid, N-ethylmaleimide, trypsin inhibitor, 1-chloro-3-tosylamido-7-amino-2-heptanone (TLCK), 1-chloro-3-tosylamido-4-phenyl-2-butanone (TPCK), trypsin inhibitor, and sodium EDTA.

Stabilizing agent, as used herein, refers to any chemical entity that, when included in a composition comprising bone matrix and/or a growth factor, enhances the osteoinductivity of the composition as measured against a specified reference sample. In most cases, the reference sample will not contain the stabilizing agent, but in all other respects will be the same as the composition with stabilizing agent. The stabilizing agent also generally has little or no osteoinductivity of its own and works either by increasing the half-life of one or more of the active entities within the composition as compared with an otherwise identical composition lacking the stabilizing agent, or by prolonging or delaying the release of an active factor. In certain embodiments, the stabilizing agent may act by providing a barrier between proteases and sugar-degrading enzymes thereby protecting the osteoinductive factors found in or on the matrix from degradation and/or release. In other embodiments, the stabilizing agent may be a chemical compound that inhibits the activity of proteases or sugar-degrading enzymes. In some embodiments, the stabilizing agent retards the access of enzymes known to release and solubilize the active factors. Half-life may be determined by immunological or enzymatic assay of a specific factor, either as attached to the matrix or extracted there from. Alternatively, measurement of an increase in osteoinductivity half-life, or measurement of the enhanced appearance of products of the osteoinductive process (e.g., bone, cartilage or osteogenic cells, products or indicators thereof) is a useful indicator of stabilizing effects for an enhanced osteoinductive matrix composition. The measurement of prolonged or delayed appearance of a strong osteoinductive response will generally be indicative of an increase in stability of a factor coupled with a delayed unmasking of the factor activity.

Superficially demineralized, as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

DETAILED DESCRIPTION

I. Introduction

Osteoinductive compositions and implants and methods for their production are provided. In various embodiments, the osteoinductive compositions may comprise one or more of partially demineralized (including surface demineralized) bone particles treated to disrupt the collagen structure, a tissue-derived material or extract, and a carrier. In some embodiments, the partially demineralized bone particles may not be treated to disrupt the collagen structure. In some embodiments, demineralized bone matrix, such as demineralized bone fibers, may be added to the treated partially demineralized bone particles. The combination of DBM and partially demineralized bone particles may then further include a tissue-derived extract and/or a carrier. Those of ordinary skill will appreciate that a variety of embodiments or versions of the invention are not specifically discussed below but are nonetheless within the scope of the present invention, as defined by the appended claims.

According to certain embodiments, partially demineralized bone particles are exposed to a treatment or condition that increases at least one biological activity of the partially demineralized bone particles. A tissue-derived extract may be added to the partially demineralized bone particles. Alternatively, or additionally, the partially demineralized bone particles may be added to a carrier. In some embodiments, the partially demineralized bone particles may function as a carrier for the tissue-derived extract. In some embodiments, the partially demineralized treated particles may be used without addition of an extract or a carrier. In some embodiments, the partially demineralized particles may not be treated.

In some embodiments, a method of producing autolyzed, antigen-extracted, allogeneic bone in the absence of protease inhibitors is provided.

FIG. 1 illustrates a method 10 for producing an osteoinductive composition in accordance with a first embodiment. As shown, the method comprises particulating bone [block 12] and surface-demineralizing the bone particles [block 14]. The surface demineralized bone particles may be treated to disrupt collagen structure of the bone [block 16]. The treatment may be done in any suitable manner and is discussed more fully below. In some embodiments, treatment of the surface demineralized bone particles [block 16] is not done. A tissue-derived extract may added to the surface-demineralized bone particles [block 18]. In some embodiments, the surface-demineralized bone particles may be combined with demineralized bone matrix, such as pressed demineralized bone fibers [block 17]. The surface-demineralized bone particles, with or without demineralized bone matrix or tissue derived extract, may be used with a delivery vehicle [block 19]. In one embodiment, the delivery vehicle may be a carrier and the composition may be added to a carrier [block 20]. In another embodiment the delivery vehicle may be a covering and the composition, including the surface-demineralized bone particles, pressed demineralized bone fibers, tissue derived extract, and/or carrier, may be provided in a covering [block 22]. The composition, including delivery vehicle in some embodiments, may be used to treat a bone defect [block 24].

In some embodiments, treatment of the surface of demineralized bone particles [block 16] may disrupt collagen and growth factors of both the exterior and the interior of the bone particles. In other embodiments, collagen and growth factors of the exterior of the bone may be left substantially intact while collagen and growth factors of the interior of the bone are disrupted.

Figure 3:
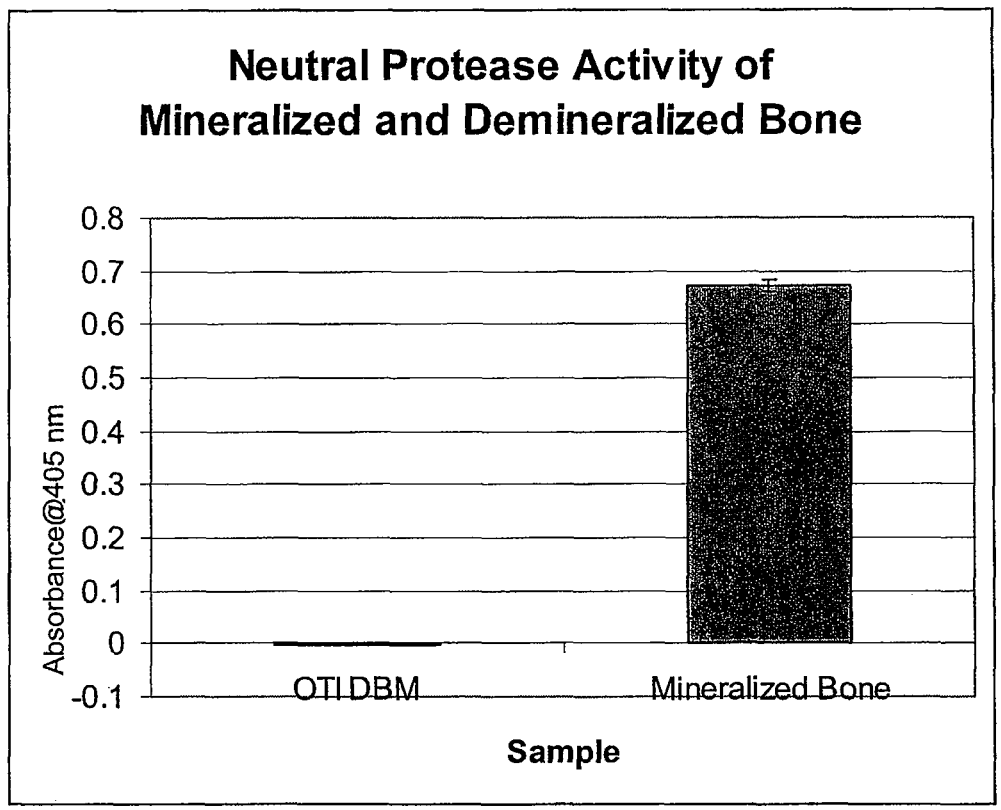
FIG. 3 illustrates a graph of neutral protease activity of mineralized and demineralized bone.

Surface demineralization of the bone substantially removes mineral and proteases from the surface of the bone. FIG. 3 is a graph showing neutral protease activity of mineralized and demineralized bone. As shown, demineralized bone has significantly lower neutral protease activity than mineralized bone. Demineralization prior to autolysis or treatment of the bone reduces protease activity on the surfaces of the particle. Accordingly, using treatment techniques that disrupt collagen and growth factors in the presence of proteases, for example, autolysis, surface collagen and growth factors are not disrupted if demineralization proceeds such treatment. In contrast, the growth factors in the mineralized portion of the bone are disrupted during such treatment. The lower protease activity of the particle surfaces maintains osteoinductive activity. Autolysis of the osteoconductive mineralized core of the particles causes the particles to exhibit reduced delayed hypersensitivity reaction. Thus, in accordance with some embodiments, a method of autolysis of bone and maintenance of osteoinductive activity in the bone without requiring use of protease inhibitors.

Figure 2:
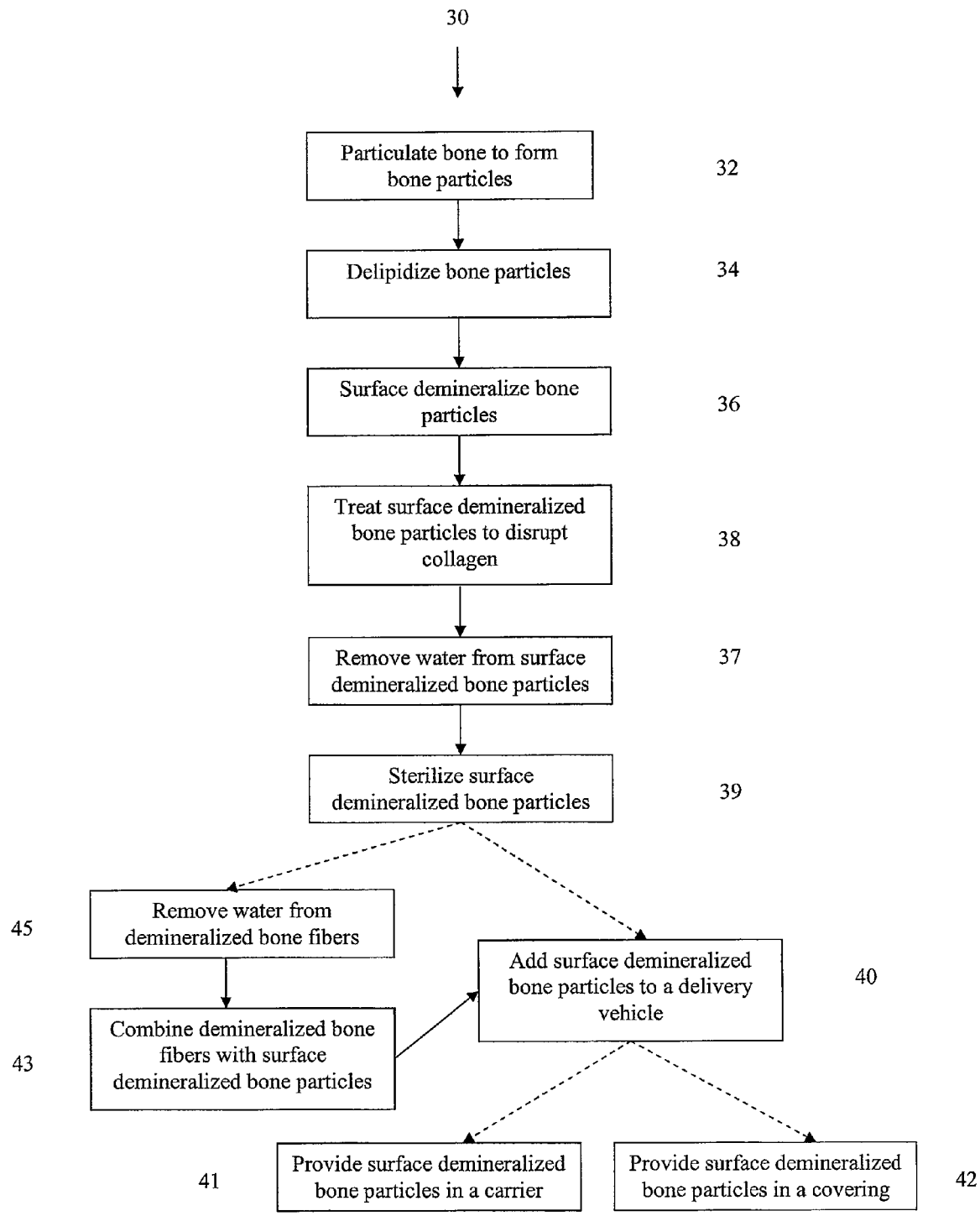
FIG. 2 illustrates a flowchart of a method for producing osteoinductive bone in the absence of protease inhibitors in accordance with one embodiment.

FIG. 2 illustrates a method 30 of producing osteoinductive bone in the absence of protease inhibitors. As shown in FIG. 2, bone particles are particulated [block 32]. The bone particles may be particulated to any suitable size ranging from microns to millimeters. In some embodiments, the particles are particulated to a size ranging from approximately 500 microns to approximately 10 mm, from approximately 500 microns to approximately 4 mm, or other size. In one embodiment, the bone particles range from between about 0.5 mm to about 15 mm in their longest dimension. The bone particles are delipidized [block 34]. Delipidizing the bones may comprise delipidizing the bone in 70% to 100% ethanol for more than about 1 hour. Delipidizing the bones may also comprise delipidizing bone in a critical or supercritical fluid such as carbon dioxide. The delipidized bone particles are surface demineralized [block 36], as described more fully below. The surface demineralized delipidized bone particles may optionally be treated to disrupt collagen by, for example, incubating in a phosphate buffer [block 38]. The incubation may be done in any suitable manner, including, for example, at a pH of approximately 7.4, at approximately 37° C. for several hours (for example, ranging from approximately 2 hours to approximately 96 hours). The particles may be treated to remove water, for example via lyophilization or critical point drying [block 37], and sterilized [block 39]. In some embodiments, removing water the particles may be done prior to treating the surface demineralized bone particles to disrupt the collagen structure. Removing water from the particles may be referred to as drying the particles or dehydrating the particles and may be done to any suitable level. Sterilization may comprise, for example, treatment with supercritical carbon dioxide. The bone particles may be used with a delivery vehicle [block 40], such as by adding to a carrier [block 41] and/or placement in a covering [block 42].

In some embodiments, demineralized bone fibers may be combined with the bone particles in a delivery vehicle [block 43]. In some embodiments, the bone fibers are formed by pressing, described below. Prior to combination with the particles, water may be removed from the bone fibers [block 45]. Drying of the pressed fibers may comprise, for example, critical point drying. U.S. Pat. No. 7,323,193 for a Method of Making Demineralized Bone Particles, herein incorporated by reference, describes suitable methods for making pressed demineralized bone fibers that may be used with the present invention.

The bone particles provided by the methods of FIG. 1 or 2 may be combined with tissue-derived extracts and/or carriers. In certain embodiments, the tissue-derived extract includes collagen type-I or collagen type-I residues. Thus, the extract may contain peptides or protein fragments that increase the osteoinductive or chondrogenic properties of the partially demineralized bone particles. Bone is made up principally of cells, and also of collagen, minerals, and other noncollagenous proteins. Bone matrices can be nondemineralized, partially demineralized, demineralized, deorganified, anorganic, or mixtures of these. DBM is comprised principally of proteins and glycoproteins, collagen being the primary protein component of DBM. While collagen is relatively stable, normally being degraded only by the relatively rare collagenase enzymes, various other proteins and active factors present in DBM are quickly degraded by enzymes present in the host. These host-derived enzymes include proteases and sugar-degrading enzymes (e.g., endo- and exoglycosidases, glycanases, glycolases, amylase, pectinases, galacatosidases, etc.). Many of the active growth factors responsible for the osteoinductive activity of DBM exist in cryptic form, in the matrix until activated. Activation can involve the change of a pre or pro function of the factor, release of the function from a second factor or entity that binds to the first growth factor, or exposing the BMPs to make them available at the outer surface of the DBM. Thus, growth factor proteins in a DBM or added to a DBM may have a limited osteoinductive effect because they are rapidly inactivated by the proteolytic environment of the implant site, or even within the DBM itself.

A number of endogenous factors that play important roles in the development and/or repair of bone and/or cartilage have been identified. BMPs such as BMP-2 and BMP-4 induce differentiation of mesenchymal cells towards cells of the osteoblastic lineage, thereby increasing the pool of mature cells, and also enhance the functions characteristic of differentiated osteoblasts. Canalis et al., *Endocrine Rev.* 24(2):218-235, 2003, herein incorporated by reference. In addition, BMPs induce endochondral ossification and chondrogenesis. BMPs act by binding to specific receptors, which results in phosphorylation of a class of proteins referred to as SMADs. Activated SMADs enter the nucleus, where they regulate transcription of particular target genes. BMPs also activate SMAD-independent pathways such as those involving Ras/MAPK signaling. Unlike most BMPs such as BMP-2 and BMP-4, certain BMPs (e.g., BMP-3) act as negative regulators (inhibitors) of osteogenesis. In addition, BMP-1 is distinct both structurally and in terms of its mechanism of action from other BMPs, which are members of the TGF-β superfamily. Unlike certain other BMPs (e.g., BMP-2, BMP-4), BMP-1 is not osteoinductive. Instead, BMP-1 is a collagenolytic protein that has also been shown to cleave chordin (an endogenous inhibitor of BMP-2 and BMP-4). Tolloid is a metalloprotease that is structurally related to BMP-1 and has proteolytic activity towards chordin. See Canalis, supra, for further details regarding the activities of BMPs and their roles in osteogenesis and chondrogenesis.

A variety of endogenous inhibitors of BMPs have been discovered in addition to chordin. These proteins act as BMP antagonists and include pseudoreceptors (e.g., Bambi) that compete with signaling receptors, inhibitory SMADs that block signaling, intracellular binding proteins that bind to activating SMADs, factors that induce ubiquitination and proteolysis of activating SMADs, and extracellular proteins that bind BMPs and prevent their binding to signaling receptors. Among the extracellular proteins are noggin, chordin, follistatin, members of the Dan/Cerberus family, and twisted gastrulation.

II. Implantable Osteoinductive/Osteoconductive Composition

An implantable osteoinductive composition and methods for preparing such composition are provided. The osteoinductive composition has an increased biological activity compared to other demineralized bone. For example, the composition may have inductivity exceeding that of from greater than one to about two to about five equivalent volumes of demineralized bone prepared by traditional, prior art methods. The osteoinductive composition may be formed into an implant and/or may be provided in a delivery vehicle.

The biological activities of the composition that may be increased include but are not limited to osteoinductive activity, osteogenic activity, chondrogenic activity, wound healing activity, neurogenic activity, contraction-inducing activity, mitosis-inducing activity, differentiation-inducing activity, chemotactic activity, angiogenic or vasculogenic activity, and exocytosis or endocytosis-inducing activity. It will be appreciated that bone formation processes frequently include a first stage of cartilage formation that creates the basic shape of the bone, which then becomes mineralized (endochondral bone formation). Thus, in many instances, chondrogenesis may be considered an early stage of osteogenesis, though of course it may also occur in other contexts.

The osteoinductive composition may comprise all or some of partially demineralized bone particles, demineralized bone fibers, a tissue-derived extract, and a delivery vehicle. The osteoinductive composition provides concentrated or enhanced osteoinductive activity. In some embodiments, the osteoinductive composition is prepared by providing partially demineralized bone, optionally treating the partially demineralized bone, extracting osteoinductive factors from tissue, and adding the extracted osteoinductive factors to the partially demineralized bone. The partially demineralized bone and extract may be added to a delivery vehicle such as a carrier or a covering. In other embodiments, the osteoinductive composition is prepared by provided partially demineralized bone particles (which may be in the form of chips), providing pressed demineralized bone fibers, and combining the partially demineralized bone particles and pressed demineralized bone fibers, for example in a delivery vehicle. The partially demineralized bone, pressed demineralized bone fibers, extract, and delivery vehicle may form an osteoimplant. The osteoimplant, when implanted in a mammalian body, can induce at the locus of the implant the full developmental cascade of endochondral bone formation including vascularization, mineralization, and bone marrow differentiation. Also, in some embodiments, the osteoinductive composition can be used as a delivery device to administer bioactive agents.

In some embodiments, the partially demineralized bone may comprise the delivery vehicle by forming a carrier. In certain embodiments, the carrier contains peptides or protein fragments that increase its osteoinductive or chondrogenic properties. In some embodiments, the carrier comprises the remaining matrix after extraction. The tissue-derived extract, for example, peptides or protein fragments, may be exogenously added to the carrier. Further, other agents may be added to the carrier and/or to the partially demineralized bone, e.g., agents that improve the osteogenic and/or chondrogenic activity of the partially demineralized bone by either transcriptional or post-transcriptional regulation of the synthesis of bone or cartilage enhancing or inhibiting factors by cells within the carrier.

III. Provide Partially Demineralized Bone

In some embodiments, demineralized bone that is substantially fully demineralized is used. In other embodiments, partially demineralized bone is used. In other embodiments, the surface demineralized bone is used. In other embodiments, nondemineralized bone may be used. In other embodiments, combinations of some of all of the above may be used. While many of the examples in this section refer to partially or surface demineralized bone, this is for illustrative purposes.

In one embodiment, the bone is partially demineralized. Referring to FIG. 1, the bone may be surface demineralized [block 14]. The partially demineralized bone may be provided in any suitable manner. Generally, the bone may be obtained utilizing methods well known in the art, e.g., allogenic donor bone. The partially demineralized bone may comprise monolithic bone, bone particles, or other bone-derived elements. In some embodiments, the partially demineralized bone comprises partially demineralized bone particles. The particles may range in size from about 0.5 mm to about 15 mm, from about 1 mm to about 10 mm, from about 1 mm to about 8 mm, from about 1 mm to about 4 mm, from about 0.5 mm to about 4 mm, or other range, in their longest dimension. Bone-derived elements can be readily obtained from donor bone by various suitable methods, e.g., as described in U.S. Pat. No. 6,616,698, incorporated herein by reference. The bone may be cortical, cancellous, or cortico-cancellous of autogenous, allogenic, xenogenic, or transgenic origin. The demineralized bone is referred to as partially demineralized for the purposes of illustration. Partially demineralized bone as used herein includes surface demineralized bone.

As will be described, the bone may be particulated, demineralized, and treated.

Demineralized bone matrix (DBM) preparations have been used for many years in orthopedic medicine to promote the formation of bone. For example, DBM has found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. The osteoinductive effect of implanted DBM compositions is thought to result from the presence of active growth factors present on the isolated collagen-based matrix.

To provide the osteoinductive composition described herein, the bone is treated to remove mineral from the bone. Generally, the bone is partially or surface demineralized. While hydrochloric acid is the industry-recognized demineralization agent of choice, the literature contains numerous reports of methods for preparing DBM (see, for example, Russell et al., *Orthopaedics* 22(5):524-53 1, May 1999; incorporated herein by reference). The partially demineralized bone may be prepared by methods known in the art or by other methods that can be developed by those of ordinary skill in the art without undue experimentation. In some instances, large fragments or even whole or monolithic bone may be demineralized. The whole or monolithic bone may be used intact or may be particulated following demineralization. In other embodiments, the bone may be particulated and then demineralized, as shown in FIG. 1.

Any suitable demineralization procedure may be used. In one demineralization procedure, the bone is subjected to an acid demineralization step followed by a defatting/disinfecting step. The bone is immersed in acid over time to effect demineralization. Acids that can be employed in this step include inorganic acids such as hydrochloric acid and as well as organic acids such as formic acid, acetic acid, peracetic acid, citric acid, propionic acid, etc. The depth of demineralization into the bone surface can be controlled by adjusting the treatment time, temperature of the demineralizing solution, concentration of the demineralizing solution, nature of the demineralizing agent, agitation intensity during treatment, pressure of the demineralizing environment, and other forces applied to the demineralizing solution or bone. The extent of demineralization may be altered or controlled by varying size of the bone or bone particles being demineralized, by varying concentration of the demineralization acid, by varying temperature, by sonicating or applying vacuum during demineralization, or other.

The demineralized bone is rinsed with sterile water and/or buffered solution(s) to remove residual amounts of acid and thereby raise the pH. A suitable defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing vegetative microorganisms and viruses. Ordinarily, at least about 10 to 40 percent by weight of water (i.e., about 60 to 90 weight percent of defatting agent such as alcohol) is present in the defatting disinfecting solution to produce optimal lipid removal and disinfection within the shortest period of time. A suitable concentration range of the defatting solution is from about 60 to about 85 weight percent alcohol. In one embodiment, the defatting solution has a concentration of about 70 weight percent alcohol.

In some embodiments, the demineralized bone comprises surface demineralized bone. Surface demineralization of bone to a depth just sufficient to expose the osteons provides bone having improved biological response while maintaining a mineralized core portion capable of sustaining mechanical loads. Depth of demineralization may be defined by size of the particle, amount of time the particle is in acid solution, concentration of the acid solution, volume of the acid solution, and/or temperature of the acid solution, and physical forces applied to the bone.

In some embodiments, the bone may be surface demineralized. The surface may be an inner surface, such as inside trabeculae or inside a Haversian canal. In other embodiments the surface may be an outer surface. In some embodiments, surface demineralized refers to the bone comprising at least one outer surface, or zone of an outer surface, that is demineralized and possessing a non-demineralized core. In some embodiments, the entirety of the surface may be partially demineralized. In other embodiments, a portion of the surface may be demineralized, such as by exposing only a portion of a particle to the demineralization process, by exposing a portion of the surface to a greater or lesser extent of the demineralization process, by masking, etc. Demineralization may be done to a certain percentage. In some embodiments, that percentage relates to weight percentage. In other embodiments, that percentage relates to percentage of the size of the bone being demineralized, or to the depth of demineralization. The depth of demineralization of the at least one outer surface thus may be viewed as a percentage of the size of the bone being demineralized or may be viewed as an absolute number.

Figure 4A:
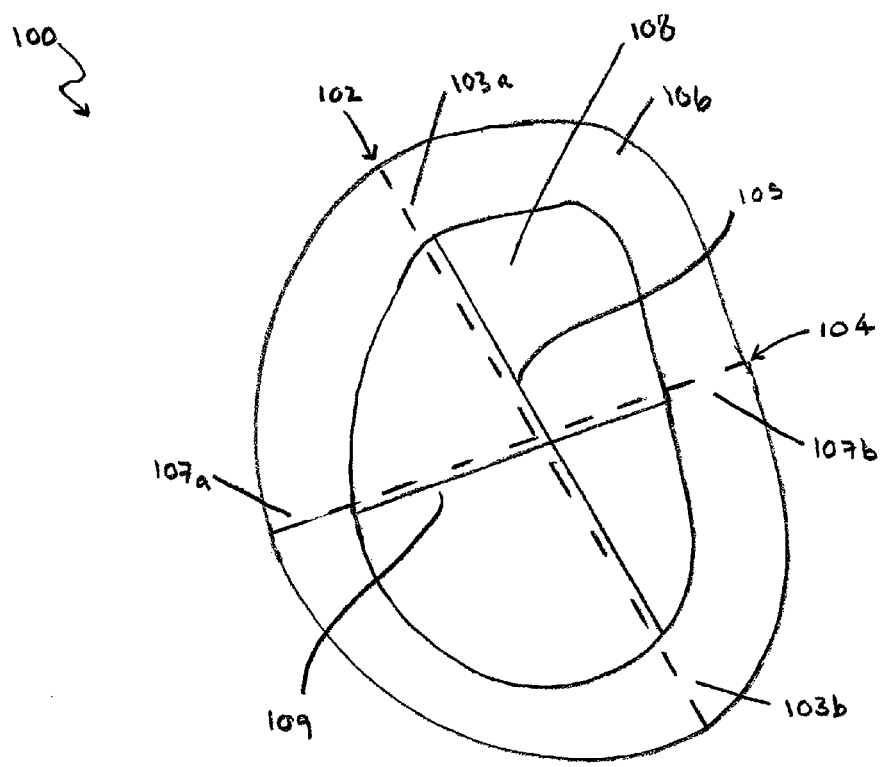
FIG. 4a illustrates a generally round bone particle wherein the bone particle has been surface demineralized in accordance with one embodiment.
Figure 4B:
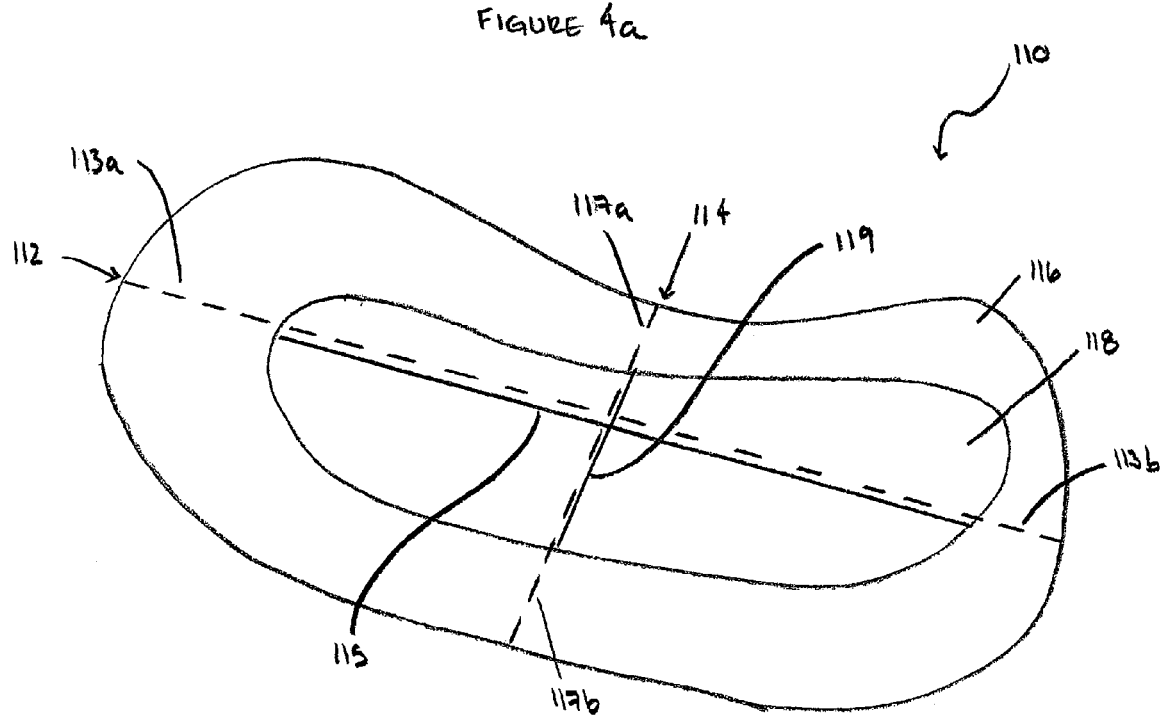
FIG. 4b illustrates an elongate bone particle wherein the bone particle has been surface demineralized in accordance with one embodiment.

Demineralization thus may be carried out to a percentage depth of the size of the bone being demineralized. FIGS. 4a and 4b illustrate surface demineralized bone particles. The bone particle 100 of FIG. 4a is substantially spherical. The bone particle 110 of FIG. 4b is somewhat elongate.

As shown, the bone particle 100 of FIG. 4a has a demineralized surface region 106 and a non-demineralized core 108. The bone particle 100 includes a length 102 along its longest dimension and a length 104 along its shortest dimension. The length 102 in the longest dimension comprises first and second demineralized portions 103a and 103b and a nondemineralized portion 105. A percentage of demineralization in the longest dimension may be determined by summing the length of the first and second demineralized portions 103a and 103b and dividing that total by the length 102 (comprising 103a, 103b and 105). The length 104 in the shortest dimension likewise comprises first and second demineralized portions 107a and 107b and a nondemineralized portion 109. A percentage of demineralization in the shortest dimension may be determined by summing the length of the first and second demineralized portions 107a and 107b and dividing that total by the length 104 (comprising 107a, 107b and 109). A total percentage demineralization may be determined by averaging the percent demineralization in the longest dimension with the percent demineralization in the shortest dimension.

As shown, the bone particle 110 of FIG. 4b has a demineralized surface region 116 and a non-demineralized core 118. The bone particle 110 includes a length 112 along its longest dimension and a length 114 along its shortest dimension. The longest dimension and shortest dimension are taken as those measuring largest and smallest, respectively, such as by a micrometer or using other by suitable manner and generally going through the center of the bone particle 110. The length 112 in the longest dimension comprises first and second demineralized portions 113a and 113b and a nondemineralized portion 115. A percentage of demineralization in the longest dimension may be determined by summing the length of the first and second demineralized portions 113a and 113b and dividing that total by the length 112 (comprising 113a, 113b, and 115). The length 114 in the shortest dimension likewise comprises first and second demineralized portions 117a and 117b and a nondemineralized portion 119. A percentage of demineralization in the shortest dimension may be determined by summing the length of the first and second demineralized portions 117a and 117b and dividing that total by the length 114 (comprising 117a, 117b, and 119). A total percentage demineralization may be determined by averaging the percent demineralization in the longest dimension with the percent demineralization in the shortest dimension.

Alternatively, percentage demineralization may be based on weight percent demineralized of total weight of the bone particle.

In some embodiments, demineralization may be carried out to a depth of, for example, at least about 100 microns. Surface demineralization may alternatively be done to a depth less than or more than about 100 microns. Generally, surface demineralization may be done to a depth of at least 50 microns, at least 100 microns, at least 200 microns, or other. Accordingly, in some embodiments, the demineralized bone comprises at least one outer surface possessing at least one demineralized zone and a non-demineralized core, wherein the demineralized zone of the outer surface of the bone may be, for example, at least about 100 microns thick. The demineralized zone may alternatively be less than or more than about 100 microns thick. The demineralized zone of the surface of the bone is osteoinductive, and therefore promotes rapid new ingrowth of native host bone tissue into an osteoimplant comprising surface demineralized bone. The osteoimplant may comprise surface demineralized monolithic bone or an aggregate of surface demineralized bone particles, and may be substantially solid, flowable, or moldable. The demineralized zone of the surface of the bone can be any surface portion.

When it is desirable to provide an osteoimplant having improved biological properties while still substantially maintaining the strength present in the osteoimplant prior to demineralization, for example where monolithic bone is used, the extent and regions of demineralization of the monolithic bone may be controlled. For example, depth of demineralization may range from at least about 100 microns to up to about 7000 microns or more, depending on the intended application and graft site. In some embodiments, the depth of demineralization is between 100 to about 5000 microns, between about 150 to about 2000 microns, or between about 200 microns to about 1000 microns. In alternative embodiments, depth of demineralization may be less than about 100 microns. Reference is made to U.S. Pat. No. 7,179,299, herein incorporated by reference for discussion of surface demineralization.

A benefit of surface demineralized bone is that the demineralized zone(s) can elastically yield under applied force while the mineralized core has strength and load bearing capacity exceeding that of demineralized bone. Thus, when the surface demineralized bone is subjected to an applied load, the demineralized zones can conform to contours of adjacent bone tissue and thereby minimize voids or spaces between the osteoimplant and adjacent bone tissue. This can be useful because host bone tissue will not grow to bridge large voids or spaces. Thus, by conforming to the contours of adjacent bone tissue, an osteoimplant comprising surface demineralized monolithic bone exhibits enhanced biological properties such as, for example, incorporation and remodeling. The non-demineralized inner core imparts mechanical strength and allows the monolithic osteoimplant to bear loads in vivo. Other non-demineralized zones provide improved tolerances when engaged with other objects such as, for example, insertion instruments, other implants or implant devices, etc. It is noted that some of these characteristics may also be exhibited by an osteoimplant comprising an aggregate of surface-demineralized bone particles.

In one embodiment, an osteoinductive composition comprising partially demineralized (or surface demineralized) bone particles is provided. The partially demineralized bone particles may, for example, range in size from 500 μm to 4 mm. In one embodiment 10-80 percent of the mineral of the mineral content of the bone is removed. When comprised of partially demineralized bone particles, the osteoinductive composition has a relatively large demineralized surface area relative to volume. The particulation further increases the rate of remodeling of the osteoinductive composition.

Mixtures of one or more types of demineralized bone-derived elements can be employed. Moreover, one or more of types of demineralized bone-derived elements can be employed in combination with non-demineralized bone-derived elements, i.e., bone-derived elements that have not been subjected to a demineralization process. Thus, e.g., the weight ratio of non-demineralized to demineralized (including fully demineralized, partially demineralized, and surface demineralized) bone elements can broadly range from less than 0:1 to about 0:1 to about approaching 1:0 or greater. Further, in some embodiments, mixtures of different types of bone-derived elements and different levels of demineralization—for example surface demineralized bone chips or particles and fully demineralized pressed bone fibers, described below—may be used. Suitable amounts can be readily determined by those skilled in the art on a case-by-case basis by routine experimentation.

As discussed, the bone may be ground or otherwise processed into particles of an appropriate size before or after demineralization. For preparing surface demineralized bone particles, the bone is particulated and then surface demineralized. In certain embodiments, the particle size is greater than 75 microns, for example ranging from about 100 to about 3000 microns, or from about 200 to about 2000 or up to greater than 10,000 microns. In some embodiments, the particle size may be below about 2.8 mm diameter, or may be between about 2.8 and about 4.0 mm diameter. After grinding the bone, the mixture may be sieved to select those particles of a desired size. In certain embodiments, the bone particles may be sieved though a 50 micron sieve, a 75 micron sieve, and or a 100 micron sieve.

Alternatively, or additionally, the bone may be particulated to form elongate particles or fibers. The bone may be particulated in any suitable manner, such as by milling or pressing. The bone fibers may comprise threads or filaments having a median length to median thickness ratio of at least about 10:1 and up to about 500:1, a median length of from about 2 mm to about 400 mm, a medium width of about 2 mm to about 5 mm, and a median thickness of from about 0.02 mm to about 2 mm. An osteoinductive composition comprising bone fibers tends to more readily retain its shape due, it would appear, to the tendency of the bone particles to become entangled with each other. The ability of the osteoinductive composition to maintain its cohesiveness and to resist erosion subsequent to being applied to an osseus defect site is advantageous since it enhances utilization of the available bone particles. Bone fibers whose median length to median thickness ratio is at least about 10:1 can be readily obtained by any one of several methods, e.g., shaving the surface of an entire bone or relatively large section of bone. Another procedure for obtaining the bone fibers, useful for pieces of bone of up to about 100 mm in length, is the Cortical Bone Shredding Mill available from Os Processing Inc., 3303 Carnegie Avenue, Cleveland, Ohio 44115. Reference is made to U.S. Pat. Nos. 5,314,476, 5,510,396, 5,507,813, and 7,323,193 herein incorporated by reference for discussion of bone fibers.

After demineralization, water optionally may be removed from the bone particles [block 37 of FIG. 2] and sterilized [block 39 of FIG. 2]. Drying may comprise lyophilization, critical point drying, vacuum drying, solvent dying, or other drying technique. Removing water from the particles may be referred to as drying the particles or dehydrating the particles and may be done to any suitable level. For example, in some embodiments 70% of the water in the bone is removed, 80% of the water in the bone is removed, 90% of the water in the bone is removed, 90% of the water in the bone is removed, 95% of the water in the bone is removed, or 98% or more of the water in the bone is removed.

Sterilization may be done in any suitable manner. In one embodiment, sterilization may comprise heat sterilizing the bone without substantially degrading biological properties of the tissue. In some embodiments, sterilization comprises gentle heating of the bone. In another embodiment, sterilization comprises heating the bone in the absence of oxygen. In a further embodiment, sterilization comprises heating the tissue in the presence of supercritical $CO_2$. U.S. patent application Ser. No. 12/140,062 to Method of Treating Tissue, filed Jun. 16, 2008, discloses methods of sterilization suitable for use with the present invention and is herein incorporated by reference for the purposes of all that is disclosed therein.

In some embodiments, the demineralized bone may further be treated, for example to at least partially remove antigens.

IV. Treat the Bone

In accordance with some embodiments, the demineralized bone may be treated such that the collagen structure of the bone is disrupted, shown at block 16 of FIG. 1. Disruption may be done in any suitable manner including, for example, heat treatment, chemical treatment, mechanical treatment, energy treatment (e.g., x-ray or radiation), and others. The collagen structure of bone comprises a triple helix form. The bone may be treated such that the triple helix form unwinds but covalent crosslinks of the structure remain intact. In general, the treatment is such that the collagen in the bone is denatured or digested to the point where protease enzymes can readily attack it, while at the same time avoiding the creation of toxic byproducts, and maintaining some of the original strength of the bone. Cortical bone treated as provided herein generally remodel faster than untreated cortical bone, and retain strength in excess of that of cancellous bone.

More specifically, collagen consists of fibrils composed of laterally aggregated, polarized tropocollagen molecules (MW 300,000). Each tropocollagen unit consists of three helically wound polypeptide α-chains around a single axis. The strands have repetitive glycine residues at every third position and numerous proline and hydroxyproline residues, with the particular amino acid sequence being characteristic of the tissue of origin. Tropocollagen units combine uniformly to create an axially repeating periodicity. Cross linkages continue to develop and collagen becomes progressively more insoluble and resistant to lysis on aging. Gelatin results when soluble tropocollagen is denatured, for example on mild heating, and the polypeptide chains become randomly dispersed. In this state the strands may readily be cleaved by a wide variety of proteases.

Various methods for disrupting the collagen structure of the demineralized bone may be used. For example, heat treatment, treatment with collagenase, other chemical treatment, mechanical treatment, or energy treatment may be employed. For the purposes of illustration, discussion is made of treating the bone after it has been particulated and demineralized. It is to be understood that the order of particulation, demineralization, and treatment may be varied. U.S. patent application Ser. No. 12/140,025, for Osteoinductive Demineralized Cancellous Bone, filed Jun. 16, 2008, is herein incorporated by reference in its entirety for the purposes of all that is disclosed therein.

Heat Treatment

In embodiments wherein treating the bone comprises heat treatment of the bone, the heat treatment may comprise, for example, gentle heating of the bone. In other embodiments, the heat treatment may comprise high temperature heating of the bone, heating the bone in the absence of oxygen, or heating the bone in the presence of supercritical fluids such as $CO_2$. Generally, any suitable form of heat treatment may be used.

Treatment of the partially demineralized bone may comprise heating the bone to temperatures ranging from approximately 40° C. to approximately 120° C. for period of time ranging from approximately 1 minute to approximately 96 hours. Heating may be done with the partially demineralized bone in a dry state, in distilled water, in a neutral buffer solution, or other. The osteoinductive composition may exhibit the ability to induce the formation of heterotopic bone in a higher order animal such as a dog, human, or sheep. In some embodiments, the osteoinductive composition may be combined with osteoinductive growth factors extracted from bone, recovered from acid used to demineralized bone, or other.

Thus, in a first embodiment, gentle heating of the bone is performed to disrupt the collagen structure of the bone. Such gentle heating denatures proteins in the bone. Heating may be performed, for example, at temperatures of approximately 60 to 70° C. Gentle heating generally does not chemically degrade the proteins in the bone. Gentle heating limits potential inflammatory response. In another embodiment, the bone may be defatted before the heat treatment to remove lipids, which are a potential thermal peroxygen compound source. Further, in some embodiments, water may be removed from the bone before heating (as at block 39 of FIG. 2).

In another embodiment, the bone is heated in the absence of oxygen. Heating in the absence of oxygen may be done in any suitable manner. For example, heating may be done using an inert atmosphere, a reducing atmosphere, a vacuum, a shielding coating (providing the coating over the tissue being done during preparation of the tissue), or other means. Heating cortical bone in the absence of oxygen produces a faster remodeling cortical bone when implanted in a vertebrate species, with a strength at least equal to that of cancellous bone. Generally, cortical bone so treated possesses at least 30% of its original strength. In some embodiments, the heating conditions may be selected such that they will result in virally inactivated bone tissue. For example, the bone may be heated at temperatures of approximately 100 to 250° C.

In some embodiments of heating in the absence of oxygen, the bone is heated in an inert atmosphere or in a reducing atmosphere. Such atmosphere acts as a protective atmosphere. Inert atmospheres may include argon, nitrogen, helium, $CO_2$ (including supercritical $CO_2$), a hydrocarbon vapor, mixtures of these gases, etc. Reducing atmospheres may comprise pure hydrogen or hydrogen mixed with an inert gas wherein the atmosphere comprises between 1 and 99 percent hydrogen. Using a reducing gas, reductive free radicals, for example from hydrogen, are produced to protect against the effects of oxidative free radicals. In various embodiments, the bone may be treated in a chamber wherein the protective atmosphere is introduced to the chamber and released after treatment. The method of release of the atmosphere may be controlled to affect the bone. For example, slow release of the atmosphere has little effect on the bone. In contrast, fast release of the atmosphere may cause the bone to expand and develop pores.

A further embodiment of heating in the absence of oxygen comprises coating the bone with a protective thermal coating. The protective thermal coating forms an oxygen barrier and, thus, the bone with the protective thermal coating may be heated in an oxygenated atmosphere. Such protective thermal coating may comprise, for example, a polymer or wax that does not react with the tissue and that forms an oxygen barrier. In one embodiment, the protective coating comprises Poly-DTE polymer. In another embodiment, the protective coating comprises a mix of Poly(lactide-co-glycolide) and Poly(ethylene glycol). The protective coating may be layered over a monolithic piece of bone or may be mixed with smaller bone elements—such as particulated bone. When mixed with particulated bone, for example, the polymer/bone mix may be molded to form an implant.

In some embodiments, the bone is surface demineralized and then incubated in a phosphate buffer. The demineralized surface of the bone remains osteoinductive. The surface-demineralized bone may then be heated without addition of enzyme inhibitors (sodium azide and iodacetic acid).

Reference is made to U.S. patent application Ser. No. 12/140,025, entitled "Osteoinductive Demineralized Cancellous Bone", filed Jun. 16, 2008, and to U.S. patent application Ser. No. 12/140,062, entitled "Method of Treating Tissue", filed Jun. 16, 2008, both herein incorporated by reference for discussion of disrupting the collagen structure of bone.

Chemical Treatment

In accordance with other embodiments, treating the bone to degrade the collagen structure of the bone comprises treating the bone with a chemical. In some embodiments, a chemical may be used to cleave simultaneously across all three chains of the collagen helix or to attack a single strand of the collagen helix. In some embodiments, the chemical cleaves Type I collagen, e.g., degrades the helical regions in native collagen, preferentially at the Y-Gly bond in the sequence Pro-Y-Gly-Pro-, where Y is most frequently a neutral amino acid. This cleavage yields products susceptible to further peptidase digestion. Any chemical or protease having one or more of these activities may be used to treat the demineralized bone.

In one embodiment, the bone is treated with a collagenase enzyme. Generally, when bone is treated with collagenase, natural degradation products are formed. Because the dense structure of the bone that inhibits remodeling may complicate an enzyme treatment process, getting the enzyme to penetrate the bone can be difficult. Physical methods such as centrifugation in an enzyme solution, or the use of a solvent such as DMSO, may thus be used.

Collagenases and their activity on collagens of various types have been extensively studied. A number of collagenase preparations are available from Worthington Biochemical Corporation, Lakewood, N.J. In general, a variety of different collagenases known in the art can be used to disrupt the collagen structure of the bone. Collagenases are classified in section 3.4.24 under the International Union of Biochemistry and Molecular Biology (NC-IUBMB) enzyme nomenclature recommendations (see, e.g., 3.4.24.3, 3.4.24.7, 3,4.24.19). The collagenase can be of eukaryotic (e.g., mammalian) or prokaryotic (bacterial) origin. Bacterial enzymes differ from mammalian collagenases in that they attack many sites along the helix.

It will be appreciated that crude collagenase preparations contain not only several collagenases, but also a sulfhydryl protease, clostripain, a trypsin-like enzyme, and an aminopeptidase. This combination of collagenolytic and proteolytic activities is effective at breaking down intercellular matrices, an essential part of tissue disassociation. Crude collagenase is inhibited by metal chelating agents such as cysteine, EDTA, or o-phenanthroline, but not DFP. It is also inhibited by α2-macroglobulin, a large plasma glycoprotein. $Ca^{2+}$ is required for enzyme activity. Therefore, it may be desirable to avoid collagenase inhibiting agents when treating bone matrix with collagenase. In addition, although the additional proteases present in some collagenase preparations may aid in breaking down tissue, they may also cause degradation of desired matrix constituents such as growth factors. Therefore, a purified collagenase that contains minimal secondary proteolytic activities along with high collagenase activity may be used. For example, a suitable collagenase preparation may contain at least 90%, at least 95%, at least 98%, or at least 99% collagenase by weight. The preparation may be essentially free of bacterial components, particularly bacterial components that could cause inflammatory or immunological reactions in a host, such as endotoxin, lipopolysaccharide, etc. Preparations having a purity greater than 99.5% can also be used. A suitable preparation is chromatographically purified CLSPA collagenase from Worthington Biochemical Corporation. Various protease inhibitors may be included that do not inhibit collagenase but that inhibit various proteases that digest BMP. For example, protease inhibitors that are known to protect BMP activity from degradation include N-ethyl maleimide, benzamidine hydrochloride, iodoacetic acid, PMSF, AEBSF, E-64. Bestatin may also be used, particularly if the preparation contains aminopeptidase activity. Any of these protease inhibitors (or others) may be provided in a composition that is used to treat the demineralized bone.

Bone morphogenetic protein I (BMP-1) is a collagenolytic protein that has also been shown to cleave chordin (an inhibitor of BMP-2 and BMP-4). Thus, BMP-I may be of use to alter the physical structure of the demineralized bone (e.g., by breaking down collagen) and/or to cleave specific inhibitory protein(s), e.g., chordin or noggin. Proteins related to any of the proteases described herein, i.e., proteins or protein fragments having the same cleavage specificity, can also be used. It will be appreciated that variants having substantial sequence identity to naturally occurring protease can be used. For example, variants at least 80% identical over at least 50%, at least 60%, at least 70%, at least 80%, at least 90%, or 100% of the length of naturally occurring protease (or any known active fragment thereof that retains cleavage specificity) when aligned for maximum identity allowing gaps can be used.

Collagen can also be broken down by treatment with a strong base, such as sodium hydroxide. Thus, in some embodiments, sodium hydroxide can be introduced to the bone to disrupt the collagen structure of the bone. Such introduction may be in the form of a solution with penetration aided by a centrifuge and/or the addition of DMSO, as is the case for an enzyme. The base will not harm the mineral component of bone; so much of the strength (especially compressive strength) is maintained.

Other chemicals, such as cyanogen bromide, may alternatively be used to alter the collagen structure of the bone.

Combinations of treatments designed to degrade collagen can be used; for example, a mild heating combined with an enzyme or base treatment; or an enzyme treatment followed by a radiation treatment. Any suitable combination of treatments, including treatments not discussed herein, may be used.

In some embodiments, the partially demineralized bone, whether provided as an aggregate of particles or a monolithic bone, may be compressed to increase its density. The structure of cancellous bone is less dense than that of cortical bone. By compressing the structure of the cancellous bone, the osteoinductive potential is increased. Compression may be done before or after addition of an extract and/or carrier to the partially demineralized bone. Compression may be achieved via any suitable mechanism. For example, compression may be achieved by mechanical means, heat, or chemical modification of the collagenous structure. Reference is made to U.S. patent application Ser. No. 11/764,026, entitled "Osteoinductive Demineralized Cancellous Bone", filed Jun. 15, 2007, herein incorporated by reference for discussion of techniques for compressing the partially demineralized bone.

V. Add Demineralized Bone Matrix

In some embodiments, demineralized bone matrix (DBM) may be added to the partially demineralized bone particles. The DBM may comprise monolithic bone, bone particles, bone fibers, or other composition of bone. Any suitable manner may be used to add the demineralized bone matrix to the partially demineralized bone particles. Any suitable ratio of demineralized bone matrix to partially demineralized bone particles may result. The various processing steps set forth herein may be performed in any suitable sequence that provides the desired results. For example, in some embodiments, the at least partially demineralized bone particles are processed, for example dried, and the demineralized bone matrix is processed, for example dried, separately from the partially demineralized bone particles. In these embodiments, the at least partially demineralized particles and the demineralized bone matrix are combined after processing. In other embodiments, the partially demineralized bone particles and the demineralized bone matrix may be combined and then processed, for example, dried, together. Other steps also may be performed in different orders, combined, or omitted, within the spirit of the present invention.

In one embodiment, the DBM comprises pressed DBM fibers. Pressed DBM fibers may comprise elongate bone particles. The elongate bone particles or bone fibers may comprise threads or filaments having a median length to median thickness ratio of at least about 10:1 and up to about 500:1, a median length of from about 2 mm to about 400 mm, a medium width of about 2 mm to about 5 mm, and a median thickness of from about 0.02 mm to about 2 mm. The DBM fibers may be pressed bone fibers.

Pressed bone fibers refers to the manner by which the bone fibers are formed. Generally, forming the bone fibers by pressing the bone, as described below, results in intact bone fibers of longer length than other methods of producing elongate bone fibers, with the bone fibers retaining more of the native collagen structure. The bone may be particulated via pressure applied to the bone, as discussed in U.S. Pat. No. 7,323,193.

The entire bone can then be demineralized or can be sectioned before demineralization. The entire bone or one or more of its sections is subjected to demineralization to reduce the inorganic content of the bone, e.g., to less than about 10% by weight, less than about 5% by weight, or less than about 1% by weight, residual calcium. Demineralization of the bone can be accomplished in accordance with known and conventional procedures, as described above.

Following demineralization, the bone is subdivided into demineralized bone fibers of desired configuration and size. One method suitable for subdividing demineralized bone stock is to subject the bone to pressing. One pressing technique comprises applying pressure to the unconstrained demineralized bone. Examples include pressing the bone using a mortar and pestle, applying a rolling/pressing motion such as is generated by one or more rolling pins, or pressing the bone pieces between flat or curved plates. In other embodiments, flat or any other suitable configuration of plate or pressing surface may be used. These flattening pressures cause the bone fibers to separate. Pressing demineralized bone in this manner provides intact natural bone collagen fibers (as opposed to composite fibers made from joined short fiber sections) that can be as long as the fibers in the demineralized bone stock from which they were obtained.

Another suitable pressing technique comprises mechanically pressing demineralized bone which is constrained within a sealed chamber having at least one aperture in its floor or bottom plate. The separated fibers extrude through the holes with the hole diameter limiting the maximum diameter of the extruded fibers. As with the unconstrained pressing method, this constrained technique results in fibers that are largely intact (as far as length is concerned) but separated bone collagen bundles.

In a combined unconstrained/constrained pressing technique that results in longer fibers by minimizing fiber breakage, the demineralized bone is first pressed into an initially separated mass of fibers while in the unconstrained condition and thereafter these fibers are constrained within the sealed chamber where pressing is continued.

In general, pressing of demineralized bone to provide demineralized bone fibers can be carried out at from less than about 1,000 psi, to about 1,000 to about 40,000 psi, or from about 5,000 to about 20,000 psi, or greater than about 40,000 psi.

Depending on the procedure employed, the demineralized bone fibers may comprise elongate bone fibers with at least about 80 weight percent, at least about 90 weight percent, or at least about 95 weight percent, of the fibers possessing a median length of from about 2 to about 300 mm or greater, for example, a median length of from about 5 to about 50 mm, a median thickness of from about 0.5 to about 15 mm, for example, a median thickness of from about 1 to about 5 mm, a median width of from about 2 to about 35 mm, for example, a median width of from about 2 to about 20 mm, and a median length to thickness ratio and/or a median length to width ratio of from about 2 to 200, for example from about 10 to about 100. In some embodiments, the mass of bone fibers can be graded or sorted into different sizes, e.g., by screening, and/or any less desirable size(s) of bone fibers that may be present can be reduced or eliminated.

The demineralized bone fibers may be dried, for example using lyophilization, critical point drying, vacuum drying, solvent dying, or other drying technique.

VI. Provide a Tissue-Derived Extract

Returning to FIG. 1, a tissue-derived extract optionally may be added, shown at block 18, to the partially demineralized bone, or, in some embodiments, to the partially demineralized bone and demineralized bone matrix. The extract may be derived from any suitable tissue, such as bone, bladder, kidney, brain, skin, or connective tissue. Further, the extract may be derived in any suitable manner. The extract may be allogeneic, autogeneic, xenogeneic, or transgenic. In embodiments wherein the extract is bone-derived, the bone may be cortical, cancellous, or corticocancellous and may be demineralized, partially demineralized, or mineralized. In some embodiments, the extract may comprise demineralized bone, partially demineralized bone, mineral derived from bone, or collagen derived from bone. In some embodiments, the tissue-derived extract may be a protein extract.

As previously discussed, in the art, demineralized bone is often particulated. Typically, such particulation comprises sieving the particles to select only particles having at least a certain size. Particles below that size fall through the sieve and are categorized as waste particles. In accordance with some embodiments, the extract is derived from such waste particles.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. The osteoinductive effect of implanted DBM compositions is thought to result from the presence of active growth factors present on the isolated collagen-based matrix.

A simple and economically viable method for extracting osteoinductive factors from bone is provided herein. It is to be appreciated that this method may be applied to other tissues. The method comprises extracting osteoinductive factors such as noncollagenous proteins (including osteogenic growth factors) from DBM using a chaotropic solvent or a detergent. The chaotropic solvent may be guanidine hydrochloride of any suitable concentration, such as 4M. The detergent may be sodium dodecylsulfate in any suitable concentration, such as 1%. The chemical used for extraction is removed in an efficient manner that preserves the biological activity of the growth factors. The biologically active components are concentrated by purifying away nonessential proteins and inhibitors of bone morphogenetic protein, and the protein extracts are then combined with a biologically compatible delivery vehicle.

Using the method described, the extraction process is optimized by using relatively low cost chaotropic agents, and relatively easy-to-remove detergents. Methods to increase the speed of renaturing the extracted proteins are further provided. Typically in the art, dialysis against water is used to remove the detergent or chaotropic agent. However, by precipitating the proteins with ethanol, acetone, ammonium sulfate, or polyethylene glycol, dialysis against water is not necessary. Further, ultrafiltration may be used, thereby also avoiding dialysis.

Generally, extracted osteoinductive factors have lower specific bone forming activity when compared to the starting material (e.g., the tissue from which the osteoinductive factors are extracted). This may be caused by protein denaturation that results from extraction. For example, when guanidine is used to extract hydrophobic osteoinductive proteins, the proteins lose their native three-dimensional conformation. As a result, unless they regain their normal shape upon removal of the guanidine, they no longer are active. The addition of chemical chaperones to the guanidine solution may prevent this protein denaturation. Suitable chemical chaperones include glycerol, trehalose, proline, glycine betaine, and dextrose, along with mixtures of these and others. These chemical chaperones enable the osteoinductive proteins to regain their native three-dimensional conformation when the guanidine is removed. They also substantially prevent protein denaturation during lyophilization.

A method for extracting osteoinductive factors from the mineral component of bone is provided to recover growth factor activity that is normally lost during the demineralization process. It is known that 4 M guanidine hydrochloride can extract osteoinductive factors from finely powdered mineralized bone. Additionally, osteoinductive factors can be recovered from the acid that is typically used to demineralized bone. These osteoinductive factors are normally lost during the demineralization process and treated as waste.

In some embodiments, the tissue-derived extract to be added to the partially demineralized bone may be derived from the acid used to demineralize bone. Growth factors may be extracted from the mineral phase of bone using, for example, the following procedure. As previously described, bone is at least partially demineralized. The bone may comprise powder, fibers, chips, or other. The bone may be demineralized in an acid, for example 1M citric acid, 2M citric acid, or 0.6N HCl, at temperatures ranging from, for example 1° C. to 28° C. for time period of for example 10 minutes to 96 hours. In one embodiment, the bone is demineralized in an acid at a temperature of 4° C. After demineralization, the acid used for demineralization contains growth factors and mineral. The acid may be dialyzed against water to cause the mineral phase and the protein growth factors to co-precipitate. This biphasic (protein and mineral) material may then be collected by filtration or centrifugation and combined with a carrier or lyophilized.

In alternative embodiments, the protein and mineral material in the acid may be separated by dialyzing the acid, also referred to as the demineralization bath, against a weak acid, for example 0.25M citric acid. In such embodiment, the mineral phase passes through the dialysis bag and the protein phase (collagen fragments, growth factors, etc.) is left within the bag. The protein phase can then be recovered by dialyzing against water and separating water soluble and water insoluble proteins from one another.

In one embodiment, the method for extracting growth factors comprises demineralizing powdered bone with dilute acid within a dialysis bag. Suitable dilute acid includes 0.05 M to 1.0 M HCl and 1M or 2M citric acid. After removing the demineralized bone, the contents of the bag may be further dialyzed against dilute acid to remove the mineral components. A volatile acid, such as acetic acid, can be used to facilitate recovery by lyophilization.

Proteases may reduce the activity of the osteoinductive factors in demineralized bone by breaking down those osteoinductive factors. This negative effect may be reduced or eliminated by adding protease inhibitors to the HCl solution. Suitable protease inhibitors include N-ethyl maleimide, benzamidine HCl, cysteine, or iodoacetic acid. Alternatively, the bone may be heated briefly to inactivate the proteases, which are relatively more heat sensitive than the growth factors. A suitable heating regimen is 5 minutes at 60° C., or 1 minute at 90° C.

Thus, mineralized bone or bone mineral recovered from demineralization acid may be used for purifying recovered proteins. The protein phase recovered from the demineralization bath may be solubilized in urea or other form of detergent solution. The bone stimulating growth factors may then be purified, for example using a hydroxyapatite affinity chromatography scheme.

In one embodiment the tissue derived extract may comprise a protein composition substantially free from inorganic components. The protein composition may comprise less than 5% inorganic components by weight. In an alternative embodiment, a protein composition comprising organic components ranging from approximately 6% to approximately 20% by weight is provided. In another embodiment, a protein composition comprising organic components ranging from approximately 21% to approximately 50% may be provided. In yet a further embodiment, a protein composition comprising organic components ranging from approximately 51% to approximately 90% may be provided. The protein composition may be recovered from acid used to demineralize bone. The protein composition may alternatively be extracted from other tissues or in other manners. The proteinaceous material of the protein composition may be purified by chromatography, electrophoresis, or other chemical or physical means. The protein composition may be combined with another material such as demineralized bone, hydroxyapatite, tricalcium phosphate (TCP), dicalcium phosphate (DCP), or other. In some embodiments, the protein composition may exhibit the ability to induce heterotopic bone formation in an athymic animal. In some embodiments the protein composition can serve as a source of collagen Type I, collagen Type I residues, and other extracellular matrix proteins that can support tissue repair processes such as angiogenesis, osteoconduction and wound healing. As the protein material has desirable handling properties when combined with water or glycerol, the protein can also serve as a carrier for a variety of bone forming matrices including partially demineralized or fully demineralized bone matrix.

In some embodiments, the tissue-derived extract may be solubilized in an appropriate medium, such as 6M urea, exposed to hydroxyapatite, TCP, DCP, mineralized bone, surface demineralized bone, or mineral recovered from acid used to demineralize bone. The protein may further be permitted to adsorb onto mineral surfaces and be washed with a solution comprising, for example, sodium phosphate ranging from approximately 1 mM to 50 mM in concentration. The proteins may then be eluted with a solution comprising, for example, sodium phosphate ranging in concentrations from between approximately 100 mM to approximately 500 mM.

With specific reference to extracts from bone, proteins in bone matrix tend to be insoluble and may associate with the bone matrix. Generally, collagens are among the most insoluble osteoinductive factors. Extraction methods may be used to increase the solubility of the osteoinductive factors to facilitate extraction of the osteoinductive factors. Generally, growth factors are hydrophobic and are not readily soluble. Thus, growth factors may be treated to improve solubility.

The solubility of demineralized bone in one or more solvents (e.g., an aqueous medium) may be changed, e.g., increased, relative, for example, to the solubility of a standard demineralized bone not exposed to the treatment. Preferably, the aqueous medium is at physiological conditions, e.g., pH, osmotic pressure, salt concentration, etc. within physiologically appropriate ranges. For example, the pH may be approximately 7.2-8.0, or preferably 7.4-7.6. The osmotic pressure may be approximately 250-350 mosm/kg, 280-300 mosm/kg, etc. More generally, the pH may be between approximately 3-11, 4-10, 5-9, 6-8.5, etc. The osmotic pressure may be between 50-500 mosm/kg, 100-350 mosm/kg, etc. The salt concentration may be approximately 100-300 mM NaCl, e.g., approximately 150 mM NaCl. The aqueous medium may be tissue culture medium, blood, extracellular fluid, etc., and the physiological conditions may be conditions such as are typically found within these fluids and/or within a body tissue such as muscle. The solubility may be increased at any temperature, e.g., room temperature, body temperature of a subject such as a human or animal, etc.

Collagenase treatment of standard human DBM increases its solubility relative to that of untreated standard human DBM. The solubility of the DBM may be increased by exposure to an appropriate treatment or condition, e.g., collagenase treatment, radiation, heat, etc. The extent to which the solubility is increased may be varied by varying the nature of the treatment (e.g., the enzyme concentration) and/or the time over which it is applied. A combination of treatments may be used. In certain embodiments, the solubility of the DBM composition is greater than that of a standard DBM composition by between 10% and 4000% percent. For example, the solubility may be greater by between 10% and 100%, 100% and 500%, 500% and 1000%, 1000% and 2000%, 2000% and 3000%, 3000% and 4000% or any other range between 10% and 4000%. The solubility may be assessed at any time following the treatment to increase the solubility of the DBM composition. For example, the DBM may be placed in aqueous medium for a period of time such as 24-48 hours, 3, 4, 5, 6, or 7 days, 10 days, 14 days, etc. The amount of DBM remaining after the period of time is quantitated (e.g., dry weight is measured) and compared with the amount that was present initially. The extent to which the amount decreases after a period of time serves as an indicator of the extent of solubilization.

In alternative embodiments, tissue-derived extracts may be derived in any suitable manner. Further, during extraction, coprecipitates may be used. Thus, for example, using bone, the bone may be treated with a chaotropic solvent such as guanidine hydrochloride. The bone and chaotropic solvent are dialyzed against water. As the chaotropic solvent decreases, it is replaced by water. Precipitates are then extracted. Coprecipitates, such as protein, collagen, collagen fragments, albumen, or protein with RGD sequences, may be extracted. The extracted osteoinductive factors and coprecipitates may then be blended into a homogenous mixture.

In one embodiment, a simplified extraction process may be used that is amenable to batch processing. K. Behnam, E. Brochmann, and S. Murray; Alkali-urea extraction of demineralized bone matrix removes noggin, an inhibitor of bone morphogenetic proteins; Connect Tissue Res. 2004, 45(4-5): 257-60.

A number of naturally occurring proteins from bone or recombinant osteoinductive factors have been described in the literature and are suitable for use in the osteoinductive composition as a tissue-derived extract. Recombinantly produced osteoinductive factors have been produced by several entities. Creative Biomolecules of Hopkinton, Mass., produces an osteoinductive factor referred to as Osteogenic Protein 1, or OP1. Genetics Institute of Cambridge, Mass., produces a series of osteoinductive factors referred to as Bone Morphogenetic Proteins 1-13 (i.e., BMP 1-13), some of which are described in U.S. Pat. Nos. 5,106,748 and 5,658,882 and in PCT Publication No. WO 96/39,170, each herein incorporated by reference. Purified osteoinductive factors have been developed by several entities. Collagen Corporation of Palo Alto, Calif., developed a purified protein mixture that is purported to have osteogenic activity, as described in U.S. Pat. Nos. 4,774,228, 4,774,322, 4,810,691, and 4,843,063, each herein incorporated by reference. Urist developed a purified protein mixture which is purported to be osteogenic, as described in U.S. Pat. Nos. 4,455,256, 4,619,989, 4,761,471, 4,789,732, and 4,795,804, each herein incorporated by reference. International Genetic Engineering, Inc. of Santa Monica, Calif., developed a purified protein mixture that is purported to be osteogenic, as described in U.S. Pat. No. 4,804,744, herein incorporated by reference.

One osteoinductive factor that may be used as a tissue-derived extract in the osteoinductive composition is described in detail in U.S. Pat. No. 5,290,763, herein incorporated by reference. This osteoinductive factor has a high osteogenic activity and degree of purity. The osteoinductive factor of the '763 patent exhibits osteoinductive activity at about 3 micrograms when deposited onto a suitable carrier and implanted subcutaneously into a rat. In one embodiment, the osteoinductive factor is an osteoinductively active mixture of proteins that exhibit the gel separation profile shown in FIG. 1 of U.S. Pat. No. 5,563,124, herein incorporated by reference.

In some embodiments, the tissue-derived extract may comprise bone stimulating growth factors, for example recovered from the mineral phase of bone. The bone stimulating growth factors may be purified using an apatite affinity chromatography scheme. Thus, mineralized or surface demineralized bone may be used as a chromatography resin. Bone mineral comprises calcium phosphate sales similar to hydroxyapatite. To use mineralized or surface demineralized bone as a chromatography resin, excess lipid and protein may be removed from the surfaces of the bone. In other embodiments, a similar scheme may be done using demineralized bone matrix as a resin. In yet further embodiments, recovered inorganic bone mineral (sintered or unsintered) may be used as the chromatography resin.

In one embodiment, the protocol for such scheme may be as follows. Mineralized bone particles, for example ranging from 100 µm to 5 mm, are prepared. The surface of the mineralized bone particles is cleaned, for example by soaking or stirring the bone particles in a dilute base such as 0.1M NaOH for several minutes. Generally, such surface cleaning removes proteins as well as lipids. In alternative embodiments, surface cleaning may be performed using supercritical $CO_2$. Growth factor extracts from the mineral phase may be solubilized in a chaotropic solvent such as 6M urea. The growth factor solution may then be mixed with the mineralized bone particles, for example, for several minutes. During such mixing, proteins having an affinity for hydroxyapatite bind to the bone surfaces. The bone-protein complex is then precipitated and the supernatant removed. The bone-protein complex may be treated to remove weakly bound proteins such as collagen fragments while retaining osteoinductive proteins (the osteoinductive proteins remain bound to the material). Such treatment may comprise treating the bone-protein complex with a 6M urea containing low concentrations of sodium phosphate. The treated bone-protein complex may be centrifuged and the supernatant aspirated. In some embodiments, the bone-protein complex may be treated with urea containing higher concentrations of sodium phosphate (e.g., 100 mM, 180 mM, or 250 mM) to release bound osteoinductive proteins. Alternatively, the bone-osteoinductive protein complex may be lyophilized and formulated with a carrier, for example for orthopedic applications. Further, the bone protein complex may be used as a growth factor microcarrier that can be distributed in a DBM macrocarrier.

Extraction may extract, for example, both osteoinductive factors and their inhibitors. If the inhibitors are extracted, the osteoinductive factors may be separated out. This may be referred to as removal of the inhibitors or concentration of the osteoinductive factors. As a general matter, both the osteoinductive factors and the inhibitors may be extracted and both the osteoinductive factors and the inhibitors may be used for forming the osteoinductive composition. Alternately, only the osteoinductive factors (and not their inhibitors) are extracted and only the osteoinductive factors are used for manufacturing the osteogenic osteoimplant. Lastly, both the osteoinductive factors and the inhibitors may be extracted and only the osteoinductive factors may be used for forming the osteoinductive composition. In some embodiments, it may be desirable to remove inhibitors or concentrate the osteoinductive factors. This is optional and may be done by any suitable method. Generally, it may be desirable to remove the inhibitors quickly without denaturing the osteoinductive factors. Reference is made to U.S. patent application Ser. Nos. 11/555,606 and 11/555,608, to which the present application claims priority and which is herein incorporated by reference for discussion of other processing that may be used. The embodiment of extraction and resultant use of osteoinductive factors with or without inhibitors is not a limiting feature of the present invention.

In some embodiments, the tissue-derived extract may be modified in one or more ways, e.g., its protein content can be augmented or modified as described in U.S. Pat. Nos. 4,743,259 and 4,902,296, the contents of which are incorporated by reference herein. The extract can be admixed with one or more optional substances such as binders, fillers, fibers, meshes, substances providing radiopacity, plasticizers, biostatic/biocidal agents, surface active agents, and the like, prior to, during, or after adding to the carrier.

VII. Add Extract to the Partially Demineralized Bone

As shown at block 18 of FIG. 1, the tissue-derived extract may be added to the partially demineralized bone, or, in some embodiments, to the partially demineralized bone and demineralized bone matrix. Such addition may be done in any suitable manner. As discussed, the tissue-derived extract may comprise extracted osteoinductive factors and possibly inhibitors. For ease of reference, unless otherwise noted, reference to osteoinductive factors refers to osteoinductive factors with or without inhibitors.

The tissue-derived extract may be added in any suitable extract dose. Generally the dosage may be from less than 1× to approximately 10×. For the purposes of this disclosure, 1× is defined as the amount of extract that may be derived from a single clinically relevant unit of tissue. For example, using bone as the tissue, for a 10 cc unit of DBM, mineralized bone, or surface demineralized bone, 1× is the amount of extract that can be derived from 10 cc of the bone.

When the extract is added to the partially demineralized bone, the partially demineralized bone may first act as a bulking means for applying a small amount of extracted material. The partially demineralized bone also may serve as a scaffold, and may aid in controlling release kinetics. Any suitable shape, size, and porosity of partially demineralized bone may be used. Rat studies show that the new bone is formed essentially having the dimensions of the device implanted. Generally, particle size influences the quantitative response of new bone; particles between 70 µm and 420 µm elicit the maximum response. However, other particle sizes may be used.

The partially demineralized bone may comprise a DBM preparation. Generally, the DBM preparation will include at least some portion of surface demineralized bone. DBM prepared by any method may be employed, including particulate or fiber-based preparations, mixtures of fiber and particulate preparations, fully or partially demineralized preparations, mixtures of fully and partially demineralized preparations, and surface demineralized preparations. See U.S. Pat. No. 6,326,018, Reddi et al., *Proc. Natl. Acad. Sci. USA* (1972) 69:1601-1605; Lewandrowski et al., *Clin. Ortho. Rel. Res.*, (1995) 317:254-262; Lewandroski et al., *J. Biomed. Mater. Res.* (1996) 31:365-372; Lewandrowski et al. *Calcified Tiss. Int.*, (1997) 61:294-297; Lewandrowski et al., *I Ortho. Res.* (1997) 15:748-756, each of which is incorporated herein by reference. Suitable demineralized bone matrix compositions are described in U.S. Pat. No. 5,507,813, herein incorporated by reference. As discussed, the bone may be particulated. In alternative embodiments, the bone may be in the form of a section that substantially retains the shape of the original bone (or a portion thereof) from which it was derived. Also useful are preparations comprising additives or carriers such as polyhydroxy compounds, polysaccharides, glycosaminoglycan proteins, nucleic acids, polymers, poloxamers, resins, clays, calcium salts, and/or derivatives thereof.

As discussed, the tissue-derived extract may be combined with the partially demineralized bone. The manner by which the tissue-derived extract is combined with the partially demineralized bone can influence the biological activity of the final composition. The tissue-derived extract may be lyophilized, resulting in a powder. In some situations, adding a powder to a bone matrix may be challenging. Thus, it may be desirable to process a powdered tissue-derived extract to form a homogenous mixture that may be more easily added to partially demineralized bone. This can impact release kinetics of any growth factors.

Thus, in a specific example, if the tissue-derived extract is lyophilized and then added to the partially demineralized bone, the solution may be inhomogeneous, with most of the tissue-derived extract concentrated on the outside of the partially demineralized bone. If the tissue-derived extract is added to very thin DBM sheets and each sheet is folded in on itself, the distribution of tissue-derived extract may be more homogenous. The sheets in such an embodiment can be very thin, on the order of microns. The sheets may comprise, for example, the partially demineralized bone mixed with a carrier, described more fully below.

Any suitable method for adding, or dispersing, the tissue-derived extract to the partially demineralized bone may be used. Generally, the procedures used to formulate or disperse the tissue-derived extract onto the partially demineralized bone are sensitive to the physical and chemical state of both the tissue-derived extract and the partially demineralized bone. In some embodiments, the extract may be precipitated directly onto the partially demineralized bone.

In one embodiment, the tissue-derived extract is blended with a bulking agent to form a homogenous mixture. This mixture is added to the partially demineralized bone. Alternatively, the tissue-derived extract may be blended with coprecipitates and this blend may be added to the partially demineralized bone.

In some embodiments, after the extract has been added to the partially demineralized bone, the partially demineralized bone may have a BMP content (BMP-2 content, BMP-4 content, BMP-7 content, TGF-beta content, IGF-II content, MMP-13 content, and/or aggregate BMP content) of at least approximately 110% that of demineralized bone without added tissue-derived extract.

Thus, in some embodiments, an osteoinductive composition comprising surface demineralized bone particles and tissue-derived extract is provided. The tissue-derived extract may be adsorbed to the surfaces of the partially demineralized bone particles. Weakly bound components may be eluted using, for example, low concentrations of sodium phosphate (for example, 5 mM to 50 mM), thereby concentrating the tissue-derived extract. For extract derived from bone, in some embodiments, analysis of the proteins bound to the surfaces of the surface demineralized bone particles indicates a ratio of Histone H2A to total protein bound elevated by a factor of 2 to 10,000 times over the normal ratio found in extracts of demineralized bone matrix or protein recovered from acid used to demineralize bone. In some embodiments, analysis of the proteins bound to the surfaces of the surface demineralized bone particles indicates a ratio of Secreted Phosphoprotein 24 to total protein bound elevated by a factor of 2 to 10,000 times over the normal ratio found in extracts of demineralized bone matrix or protein recovered from acid used to demineralize bone. In some embodiments, analysis of the proteins bound to the surfaces of the surface demineralized bone particles indicates a ratio of BMP-2 to total protein bound elevated by a factor of 2 to 10,000 times over the normal ratio found in extracts of demineralized bone matrix or protein recovered from acid used to demineralize bone. In some embodiments, analysis of the proteins bound to the surfaces of the surface demineralized bone particles indicates a ratio of BMP-4 to total protein bound elevated by a factor of 2 to 10,000 times over the normal ratio found in extracts of demineralized bone matrix or protein recovered from acid used to demineralize bone. In some embodiments, analysis of the proteins bound to the surfaces of the surface demineralized bone particles indicates a ratio of TGF-Beta to total protein bound elevated by a factor of 2 to 10,000 times over the normal ratio found in extracts of demineralized bone matrix or protein recovered from acid used to demineralize bone.

In some embodiments, no tissue-derived extract may be added to the partially demineralized bone.

VIII. Add Partially Demineralized Bone to Delivery Vehicle

As shown at block 19 of FIG. 1, the partially demineralized bone, with or without a tissue-derived extract and/or demineralized bone matrix, optionally may be used with a delivery vehicle. In one embodiment, such delivery vehicle may be a carrier to which the partially demineralized bone is added [block 20 of FIG. 1]. In another embodiment, such delivery vehicle may be a covering in which the partially demineralized bone is provided [block 22 of FIG. 1]. In other embodiments, a carrier and a covering both may be used. The partially demineralized bone and delivery vehicle together form an osteoimplant useful in clinical applications.

Add Partially Demineralized Bone to Carrier

The carrier may be formulated to impart specific handling characteristics to the composition. For example, in some embodiments, the carrier may be formulated such that the composition substantially retains its shape in fluids such as blood, serum, or water. Such carrier may comprise, for example, a combination of alginate and chitosan, an acidic alginate (a combination of alginate and an acid), or other.

Suitable carriers include DBM, including surface demineralized bone; mineralized bone; nondemineralized cancellous scaffolds; demineralized cancellous scaffolds; cancellous chips; particulate, demineralized, guanidine extracted, species-specific (allogenic) bone; specially treated particulate, protein extracted, demineralized, xenogenic bone; collagen; synthetic hydroxyapatites; synthetic calcium phosphate materials; tricalcium phosphate, sintered hydroxyapatite, settable hydroxyapatite; polylactide polymers; polyglycolide polymers, polylactide-co-glycolide copolymers; tyrosine polycarbonate; calcium sulfate; collagen sheets; settable calcium phosphate; polymeric cements; settable poly vinyl alcohols, polyurethanes; resorbable polymers; and other large polymers; liquid settable polymers; and other biocompatible settable materials. The carrier may further comprise a polyol (including glycerol or other polyhydroxy compound), a polysaccharide (including starches), a hydrogel (including alginate, chitosan, dextran, pluronics, N,O-carboxymethyl-chitosan glucosamine (NOCC)), hydrolyzed cellulose, or a polymer (including polyethylene glycol). In embodiments wherein chitosan is used as a carrier, the chitosan may be dissolved using known methods including in water, in mildly acidic aqueous solutions, in acidic solutions, etc. The carrier may further comprise a hydrogel such as hyaluronic acid, dextran, Pluronic block copolymers of polyethylene oxide and polypropylene, and others. Suitable polyhydroxy compounds include such classes of compounds as acyclic polyhydric alcohols, non-reducing sugars, sugar alcohols, sugar acids, monosaccharides, disaccharides, water-soluble or water dispersible oligosaccharides, polysaccharides and known derivatives of the foregoing. An example carrier comprises glyceryl monolaurate dissolved in glycerol or a 4:1 to 1:4 weight mixture of glycerol and propylene glycol. Reference is made to U.S. Pat. No. 5,314,476 for other carriers including polyhydroxy carriers, to U.S. Pat. No. 6,884,778 for biocompatible macromere that may be used as carriers, and to U.S. Patent Publication No. 2003/0152548 for cross-linkable monomers that may be used as carriers, all herein incorporated by reference. Settable materials may be used, and they may set up either in situ, or prior to implantation. In embodiments where alginate salt (alginate sodium) is used as a settable carrier, the alginate sodium may be dissolved in water with mild acids. After adding partially demineralized bone, including surface demineralized bone, a reaction may occur between acid in alginate solution and minerals in bone to release calcium ions, which may cross-link alginate to help set the formulation. Optionally, xenogenic bone powder carriers also may be treated with proteases such as trypsin. Xenogenic carriers may be treated with one or more fibril modifying agents to increase the intraparticle intrusion volume (porosity) and surface area. Useful agents include solvents such as dichloromethane, trichloroacetic acid, acetonitrile and acids such as trifluoroacetic acid and hydrogen fluoride. The choice of carrier may depend on the desired characteristics of the composition. In some embodiments, a lubricant, such as water, glycerol, or polyethylene glycol may be added.

In some embodiments, the osteoinductive composition may comprise surface demineralized bone particles, demineralized bone matrix, tissue-derived extract such as collagenous extract, and glycerol. The osteoinductive composition may be configured to be moldable, extrudable, or substantially solid. The osteoinductive composition may be configured to substantially retain its shape in water for a period of time.

Any suitable shape, size, and porosity of carrier may be used. In some embodiments, the carrier may be settable and/or injectable. Such carrier may be, for example, a polymeric cement, a settable calcium phosphate, a settable poly vinyl alcohol, a polyurethane, or a liquid settable polymer. Suitable settable calcium phosphates are disclosed in U.S. Pat. Nos. 5,336,264 and 6,953,594, herein incorporated by reference. Hydrogel carriers may additionally impart improved spatial properties, such as handling and packing properties, to the osteoconductive composition. An injectable carrier may be desirable where the composition is used with a covering. Generally, the carrier may have several functions. In some embodiments, it carries the tissue-derived extract and partially demineralized bone and allows appropriate release kinetics. The carrier may also accommodate each step of the cellular response during bone development, and in some cases protect the tissue-derived extract from nonspecific proteolysis. In addition, selected materials must be biocompatible in vivo and optionally biodegradable. In some uses, the carrier acts as a temporary scaffold until replaced by new bone. Polylactic acid (PLA), polyglycolic acid (PGA), and various combinations have different dissolution rates in vivo. In bone, the dissolution rates can vary according to whether the composition is placed in cortical or trabecular bone.

The carrier may comprise a shape-retaining solid made of loosely adhered particulate material, e.g., with collagen. It may alternatively comprise a molded, porous solid, a monolithic solid, or an aggregate of close-packed particles held in place by surrounding tissue. Masticated muscle or other tissue may also be used. Large allogenic bone implants may act as a carrier, for example where their marrow cavities are cleaned and packed with particles and the osteoinductive factors.

In one embodiment, the osteoinductive composition induces endochondral bone formation reliably and reproducibly in a mammalian body. The carrier may comprise particles of porous materials. The pores may be of a dimension to permit progenitor cell migration into the carrier and subsequent differentiation and proliferation. The particle size thus may be within the range of approximately 70 µm to approximately 850 µm, from 70 µm to approximately 420 µm, or from approximately 150 µm to approximately 420 µm. It may be fabricated by close packing particulate material into a shape spanning the bone defect, or by otherwise structuring as desired a material that is biocompatible, and preferably biodegradable in vivo to serve as a "temporary scaffold" and substratum for recruitment of migratory progenitor cells, and as a base for their subsequent anchoring and proliferation. For such embodiments, useful carrier materials include collagen; homopolymers or copolymers of glycolic acid, lactic acid, and butyric acid, including derivatives thereof; and ceramics, such as hydroxyapatite, tricalcium phosphate and other calcium phosphates. Combinations of these carrier materials also may be used.

One way to protect small size particles from cellular ingestion and/or to provide a diffusion barrier is to embed them in a monolithic bioabsorbable matrix, and then fragment the particle-containing monolithic matrix into particle sizes greater than 70 microns, for example, greater than 100 microns, or greater than 150 microns in their smallest dimension. Suitable matrices for embedding small partially demineralized particles include biocompatible polymers and setting calcium phosphate cements. Generally the particulate partially demineralized bone/polymer weight ratio will range from about 1:5 to about 1:3. In the case of calcium phosphate, the partially demineralized bone will be present up to 75% by weight. Particulation of a monolith can be accomplished by conventional milling or grinding, or through the use of cryomilling, or freezing followed by pulverization. In one embodiment, partially demineralized bone particles are embedded in a resorbable polymer. In a further embodiment, partially demineralized bone particles are embedded in one of the setting calcium phosphates known to the art.

The carrier may comprise a number of materials in combination, some or all of which may be in the form of fibers and/or particles. The carrier may comprise calcium phosphates. Driessens et al. "Calcium phosphate bone cements," Wise, D. L., Ed., *Encyclopedic Handbook of Biomaterials and Bioengineering, Part B, Applications* New York: Marcel Decker; Elliott, *Structure and Chemistry of the Apatites and Other Calcium Phosphates* Elsevier, Amsterdam, 1994, each of which is herein incorporated by reference. Calcium phosphate matrices include, but are not limited to, dicalcium phosphate dihydrate, monetite, tricalcium phospate, tetracalcium phosphate, hydroxyapatite, nanocrystalline hydroxyapatite, poorly crystalline hydroxyapatite, substituted hydroxyapatite, and calcium deficient hydroxyapatites.

In one embodiment, the carrier comprises an osteoinductive material such as a mineralized particulated material, osteoinductive growth factors, or partially demineralized bone. The mineralized particulated material may be TCP, hydroxyapatite, mineral recovered from bone, cancellous chips, cortical chips, surface demineralized bone, or other material. The osteoinductive material may be combined with a further carrier such as starch or glycerol. Accordingly, in some embodiments, the partially demineralized bone may act as a carrier for the tissue-derived extract.

The osteoinductive composition, comprising partially demineralized bone and, in some embodiments, tissue-derived extract and carrier, may be completely insoluble or may be slowly solubilized after implantation. Following implantation, the composition may resorb or degrade, remaining substantially intact for at least one to seven days, or for two or four weeks or longer and often longer than 60 days. The composition may thus be resorbed prior to one week, two weeks, three weeks, or other, permitting the entry of bone healing cells.

In various embodiments, the partially demineralized bone may be bonded together to provide a solid, coherent aggregate through engagement with particles of binding agent present on the surfaces of the partially demineralized bone. Reference is made to U.S. Pat. Nos. 6,696,073, 6,478,825, 6,440,444, and 6,294,187, and to U.S. Patent Publications Nos. 2006/0216323 and 2005/0251267, all herein incorporated by reference.

Provide Partially Demineralized Bone in Covering

As shown in block 22 of FIG. 1, in some embodiments the composition, including the surface-demineralized bone particles, pressed demineralized bone fibers, tissue derived extract, and/or carrier, may be provided in a containment covering, such as a porous mesh, to provide a delivery system. Generally, the covering may be biocompatible and resorbable.

In some embodiments, surface demineralized bone particles, and optionally demineralized bone fibers, may be provided in a covering such that the covering provides a focus or concentration of biological activity and maintains the surface demineralized bone particles and demineralized bone fibers in spatial proximity to one another, possibly to provide a synergistic effect. The covering further may control availability of the surface demineralized bone particles and demineralized bone fibers to cells and tissues of a surgical site over time. In some embodiments, the delivery system may be used for delivery through a limited opening, such as in minimally invasive surgery or mini-open access. In some embodiments, the delivery system may be used to deliver morselized or particulated materials (the substance provided in the covering) in pre-measured amounts.

The covering may have a single compartment or may have a plurality of compartments. Thus, in one embodiment, the covering comprises first and second compartments. The surface demineralized bone particles may be provided in the first compartment and the demineralized bone fibers may be provided in the second compartment. The second compartment may be adjacent, apart from, inside, or surrounding the first compartment. In alternative embodiments, a blend of surface demineralized particles, demineralized bone fibers, tissue-derived extract, and/or other materials may be provided in either or both of first compartment and the second compartment.

In use, the partially demineralized bone particles, and demineralized bone matrix if provided, may be placed in the covering prior to implantation of the covering in the body. In alternative embodiments, the covering may be implanted in the body and the partially demineralized bone particles, and demineralized bone matrix if provided, may be placed in the covering thereafter.

In various embodiments, the covering may comprise a polymer (such as polyalkylenes (e.g., polyethylenes, polypropylenes, etc.), polyamides, polyesters, polyurethanes, poly(lactic acid-glycolic acid), poly(lactic acid), poly (glycolic acid), poly(glaxanone), poly(orthoesters), poly(pyrolicacid), poly(phosphazenes), L-co-G, etc.), other bioabsorbable polymer such as Dacron or other known surgical plastics, a natural biologically derived material such as collagen, a ceramic (with bone-growth enhancers, hydroxyapatite, etc.), PEEK (polyether-etherketone), desicated biodegradable material, metal, composite materials, a biocompatible textile (e.g., cotton, silk, linen), or other. In one embodiment, the containment covering is formed as a long tube-like covering and may be used with minimally invasive techniques.

IX. Form an Implant

The osteoimplant resulting from the partially demineralized bone, demineralized bone matrix, tissue-derived extract, and/or carrier may be flowable, have a putty or gel-like consistency, may be shaped or molded, may be provided as a slurry, may be deformable, and/or may comprise substantially dry pieces held together in a covering. The osteoimplant may comprise a monolithic bone or may comprise an aggregate of smaller bone elements. The osteoimplant may assume a determined or regular form or configuration such as a sheet, plate, disk, tunnel, cone, or tube, to name but a few. Prefabricated geometry may include, but is not limited to, a crescent apron for single site use, an I-shape to be placed between teeth for intra-bony defects, a rectangular bib for defects involving both the buccal and lingual alveolar ridges, neutralization plates, reconstructive plates, buttress plates, T-buttress plates, spoon plates, clover leaf plates, condylar plates, compression plates, bridge plates, or wave plates. Partial tubular as well as flat plates can be fabricated from the osteoimplant. Such plates may include such conformations as, e.g., concave contoured, bowl shaped, or defect shaped. The osteoimplant can be machined or shaped by any suitable mechanical shaping means. Computerized modeling can provide for the intricately-shaped three-dimensional architecture of an osteoimplant custom-fitted to the bone repair site with great precision. In embodiments wherein the osteoimplant is shaped or moldable, the implant may retain coherence in fluids.

Accordingly, the osteoinductive composition, especially when comprising as an aggregate of particles, may be subjected to a configuring step to form an osteoimplant. The configuring step can be employed using conventional equipment known to those skilled in the art to produce a wide variety of geometries, e.g., concave or convex surfaces, stepped surfaces, cylindrical dowels, wedges, blocks, screws, and the like. A surgically implantable material fabricated from elongated bone particles that have been demineralized, which may be shaped as a sheet, and processes for fabricating shaped materials from demineralized bone particles is disclosed in U.S. Pat. Nos. 5,507,813 and 6,436,138, respectively, the contents of which are herein incorporated by reference. Suitable sheets include those sold under the trade name Grafton® DBM Flex, which must be wetted/hydrated prior to use to be useful for implantation. Such sheets have recently been reported as effective in seeding human bone marrow stromal cells (BMSCs), which may be useful in the repair of large bone defects. Kasten et al., "Comparison of Human Bone Marrow Stromal Cells Seeded on Calcium-Deficient Hydroxyapatite, Betatricalcium Phosphate and Demineralized Bone Matrix," *Biomaterials*, 24(15):2593-603, 2003. Also useful are demineralized bone and other matrix preparations comprising additives or carriers such as binders, fillers, plasticizers, wetting agents, surface active agents, biostatic agents, biocidal agents, and the like. Some exemplary additives and carriers include polyhydroxy compounds, polysaccharides, glycosaminoglycan proteins, nucleic acids, polymers, poloxamers, resins, clays, calcium salts, and/or derivatives thereof.

In some embodiments, the osteoinductive composition may have improved spatial properties, such as material handling and packing properties. Unlike DBM, surface demineralized or mineralized particles do not generally entangle and hold together. Tissue-derived extracts having large amounts of collagen type I or collagen type I residues, for example a collagenous extract, can impart handling and packing properties to surface demineralized bone particles. Thus, an osteoinductive composition comprising surface demineralized bone particles and such tissue-derived extract generally may have better remodeling properties than surface demineralized bone alone. The improved remodeling properties can further be enhanced by a carrier. In some embodiments, the partially demineralized bone particles may be forced into close proximity, resulting in better osteoconduction. Some carriers may be especially suited for providing improved material handling and packing properties. These include, for example hydrogels such as chitosan and fast resorbing formulations of L-co-G. In some embodiments, the osteoinductive composition may comprise partially or fully demineralized bone particles having an improved packing efficiency.

X. Formulation

The osteoinductive composition, the delivery vehicle (including carrier or covering), or the osteoimplant may be formulated for a particular use. The formulation may be used to alter the physical, biological, or chemical properties of the composition or the carrier. A physician would readily be able to determine the formulation needed for a particular application, taking into account such factors as the type of injury, the site of injury, the patient's health, and the risk of infection. In various embodiments, the osteoinductive composition may comprise, for example less than approximately 0.5% water, less than approximately 1% water, or less than approximately 5% water.

Osteoinductive compositions or osteoimplants therefore may be prepared to have selected resorption/loss of osteoinductivity rates, or even to have different rates in different portions of an implant. For example, the formulation process may include the selection of partially demineralized particles of a particular size or composition, combined with the selection of a particular stabilizing agent or agents, and the amounts of such agents.

In one example, an osteoimplant may be provided whose tissue-derived extract comprises osteoinductive factors that are active in a relatively constant amount over a given period of time. An osteoimplant comprising factors with longer half-lives can be prepared using a less biodegradable polymer or a larger amount (e.g., a thicker coating) of polymeric compound. Alternatively or additionally, the particle size of the partially demineralized bone may be important in determining the half-life of the osteoimplant. In certain embodiments, an osteoinductive composition may include a mixture of particles, each with a different half-life. Such a mixture could provide the steady or possible unmasking of osteoinductive factors over an extended period of time ranging from days to weeks to months depending on the needs of the injury. Compositions such as this can be formulated to stimulate bone growth in a human patient comparable to the bone growth induced by treatment with 10 μg of rhBMP on a collagen sponge, and preferably comparable to 100 μg, and most preferably 1-10 mg rhBMP. When the degradation of the osteoimplant is of concern, it may be desirable to test the shelf-life of the osteoimplant to determine shelf-life at, for example, 1, 2, or 3 years. This may be done by storing the osteoimplant at, for example, room temperature or, for accelerated testing, 38° C., and periodically checking the inductivity of the osteoimplant. Reference is made to PCT/US05/003092, which is hereby incorporated by reference herein. Implants with enhanced shelf lives may retain more than about 75% and about 80% of their osteoinductivity after as long as, or longer than, three years.

Physical properties such as deformability and viscosity of the carrier may also be chosen depending on the particular clinical application. The partially demineralized bone may be mixed with other materials and factors to improve other characteristics of the implant. For example, the partially demineralized bone may be mixed with other agents to improve wound healing. These agents may include drugs, proteins, peptides, polynucleotides, solvents, chemical compounds, and biological molecules.

Further, the composition may be formulated to be settable and/or injectable. Thus, for example, the composition may be injectable through a 10-gauge, a 12-gauge, or an 18-gauge needle.

Accordingly, in some embodiments the composition may be substantially solid pieces, rubbery, rubbery with chunks, stiff (as freeze-dried), stiff with chunks, putty, paste, flowable, or injectable. The term "flowable" in this context applies to compositions whose consistencies range from those which can be described as shape-sustaining but readily deformable, e.g., those which behave like putty, to those which are runny. Specific forms of flowable bone powder compositions include cakes, pastes, creams and fillers. Reference is made to U.S. Pat. No. 5,290,558, herein incorporated by reference in its entirety, for discussion of flowable materials.

Also as previously discussed, the osteoinductive composition may be formed into various shapes and configurations, including rods, strings, sheets, weaves, solids, cones, discs, fibers, and wedges. Such shapes may result from a monolithic bone piece or an aggregate of bone particles. In certain embodiments, the shape and size of the partially demineralized bone affect the time course of osteoinductivity. For example, in a cone or wedge shape, the tapered end will result in osteoinductivity shortly after implantation of the osteoimplant, whereas the thicker end will lead to osteoinductivity later in the healing process (hours to days to weeks later). In certain embodiments of osteoimplants comprising an aggregate of bone particles, the particles have a length of greater than 2 mm, greater than 1.5 mm, greater than 1 mm, greater than 500 microns, or greater than 200 microns across its widest dimension. Also, larger particle size will induce bone formation over a longer time course than smaller particles. Particles of different characteristics (e.g., composition, size, shape) may be used in the formation of these different shapes and configurations. For example, in a sheet of partially demineralized bone, a layer of long half-life particles may be alternated between layers of shorter half-life particles. See U.S. Pat. No. 5,899,939, herein incorporated by reference, for suitable examples. In a weave, strands composed of short half-life particles may be woven together with strands of longer half-lives.

In one embodiment, fibrous partially demineralized bone may be shaped into a matrix form as described in U.S. Pat. No. 5,507,813, herein incorporated by reference. The shaped partially demineralized bone may then be embedded within a diffusion barrier type matrix, such that a portion of the matrix is left exposed free of the matrix material. Suitable blocking matrices are starch, phosphatidyl choline, tyrosine polycarbonates, tyrosine polyarylates, polylactides, polygalactides, or other resorbable polymers or copolymers. Devices prepared in this way from these matrices have a combination of immediate and longer lasting osteoinductive properties and are particularly useful in promoting bone mass formation in human posterolateral spine fusion indications.

In another embodiment, carriers having a pre-selected three-dimensional shape may be prepared by repeated application of individual layers of partially demineralized bone, for example by 3-D printing as described by U.S. Pat. Nos. 5,490,962, 5,518,680, and 5,807,437, each incorporated herein by reference. Different layers may comprise individual stabilized partially demineralized bone preparations, or alternatively may comprise partially demineralized bone layers treated with stabilizing agents after deposition of multiple layers.

In the process of preparing the osteoimplant, the materials may be produced entirely aseptically or be sterilized to eliminate any infectious agents such as HIV, hepatitis B, or hepatitis C. The sterilization may be accomplished using antibiotics, irradiation, chemical sterilization (e.g., ethylene oxide), or thermal sterilization. Other methods known in the art of preparing DBM such as defatting, sonication, and lyophilization may also be used in preparing a DBM carrier. Since the biological activity of demineralized bone is known to be detrimentally affected by most terminal sterilization processes, care must be taken when sterilizing the inventive compositions.

XI. Optional Additives

Optionally, other additives may be included in the osteoconductive composition. It will be appreciated that the amount of additive used will vary depending upon the type of additive, the specific activity of the particular additive preparation employed, and the intended use of the composition. The desired amount is readily determinable by the user.

Any of a variety of medically and/or surgically useful optional substances can be incorporated in, or associated with, the osteoinductive factors either before, during, or after preparation of the osteoinductive composition. Thus, for example when demineralized bone particles are used to form the material, one or more of such substances may be introduced into the demineralized bone particles, for example, by soaking or immersing the bone particles in a solution or dispersion of the desired substance(s).

Medically/surgically useful substances that can be readily combined with the partially demineralized bone include, for example, collagen, insoluble collagen derivatives, etc., and soluble solids and/or liquids dissolved therein, e.g., antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamicin, etc.; biocidal/biostatic sugars such as dextroal, glucose, etc.; amino acids, peptides, vitamins, inorganic elements, co-factors for protein synthesis; hormones; endocrine tissue or tissue fragments; synthesizers; enzymes such as collagenase, peptidases, oxidases, etc.; polymer cell scaffolds with parenchymal cells; angiogenic drugs and polymeric carriers containing such drugs; collagen lattices; antigenic agents; cytoskeletal agents; cartilage fragments, living cells such as chondrocytes, bone marrow cells, mesenchymal stem cells, natural extracts, tissue transplants, bone, demineralized bone powder, autogenous tissues such blood, serum, soft tissue, bone marrow, etc.; bioadhesives, bone morphogenic proteins (BMPs), angiogenic factors, transforming growth factor (TGF-beta), insulin-like growth factor (IGF-1); growth hormones such as somatotropin; bone digestors; antitumor agents; immuno-suppressants; permeation enhancers, e.g., fatty acid esters such as laureate, myristate and stearate monoesters of polyethylene glycol, enamine derivatives, alpha-keto aldehydes, etc.; and, nucleic acids. The amounts of such optionally added substances can vary widely with optimum levels being readily determined in a specific case by routine experimentation.

Bone regeneration involves a multitude of cells (e.g. cartilage, fibroblasts, endothelial, etc.) besides osteoblasts. Stem cells may be combined with the partially demineralized bone. Accordingly, the osteoinductive composition may be used to deliver stem cells, which offers the potential to give rise to different types of cells in the bone repair process In certain embodiments, the additive is adsorbed to or otherwise associated with the osteoinductive composition. The additive may be associated with the osteoinductive composition through specific or non-specific interactions, or covalent or noncovalent interactions. Examples of specific interactions include those between a ligand and a receptor, an epitope and an antibody, etc. Examples of nonspecific interactions include hydrophobic interactions, electrostatic interactions, magnetic interactions, dipole interactions, van der Waals interactions, hydrogen bonding, etc. In certain embodiments, the additive is attached to the osteoinductive composition, for example, to the carrier, using a linker so that the additive is free to associate with its receptor or site of action in vivo. In other embodiments the additive is either covalently or non-covalently attached to the carrier. In certain embodiments, the additive may be attached to a chemical compound such as a peptide that is recognized by the carrier. In another embodiment, the additive is attached to an antibody, or fragment thereof, that recognizes an epitope found within the carrier. In certain embodiments at least additives are attached to the osteoimplant. In other embodiments at least three additives are attached to the osteoinductive composition. An additive may be provided within the osteoinductive composition in a sustained release format. For example, the additive may be encapsulated within biodegradable nanospheres, microspheres, etc.

It will be understood by those skilled in the art that the lists of optional substances herewith included are not intended to be exhaustive and that other materials may be admixed with bone-derived elements within the practice of the present invention.

In one embodiment, the osteoconductive composition further comprises a cell such as an osteogenic cell or a stem cell. In various embodiments, the additive may comprise radiopaque substances, angiogenesis promoting materials, bioactive agents, osteoinducing agents, or other. Reference is made to U.S. patent application Ser. Nos. 11/555,606 and 11/555,608 for specific discussion of possible additives.

XII. Assessment of Osteogenic Activity

Any suitable manner for assessing osteogenic activity may be used. Generally, the more closely the manner of assessing osteoinductivity correlates with the anticipated use of the osteoinductive composition, the more predictive the results will be of how the osteoinductive composition will perform in a human. Thus, for example, a sheep vertebral model may be used to assess osteogenic activity of the osteoinductive composition.

In various embodiments, the osteoinductive composition may have an inductivity exceeding that of between 2 and 20 volumes of mineralized bone that is prepared into demineralized bone. For example, the osteoinductive composition may have an inductivity exceeding that of approximately five volumes of mineralized bone that is prepared into demineralized bone. In some embodiments, one gram of the osteoinductive composition may have inductivity exceeding that of demineralized bone prepared from five grams of mineralized allograft bone.

Induction of bone formation can be determined by a histological evaluation showing the de novo formation of bone with accompanying osteoblasts, osteoclasts, and osteoid matrix. For example, osteoinductive activity of an osteoinductive factor can be demonstrated by a test using a substrate onto which material to be tested is deposited. The substrate with deposited material is implanted subcutaneously in a test animal. The implant is subsequently removed and examined microscopically for the presence of bone formation including the presence of osteoblasts, osteoclasts, and osteoid matrix. A suitable procedure for assessing osteoinductive activity is illustrated in Example 5 of U.S. Pat. No. 5,290,763, herein incorporated by reference. Although there is no generally accepted scale of evaluating the degree of osteogenic activity, certain factors are widely recognized as indicating bone formation. Such factors are referenced in the scale of 0-8 which is provided in Table 3 of example 1 of U.S. Pat. No. 5,563,124, herein incorporated by reference. The 0-4 portion of this scale corresponds to the scoring system described in U.S. Pat. No. 5,290,763, which is limited to scores of 0-4. The remaining portion of the scale, scores 5-8, references additional levels of maturation of bone formation. The expanded scale also includes consideration of resorption of collagen, a factor which is not described in the '763 patent. Osteoinductivity may be assessed in tissue culture, e.g. as the ability to induce an osteogenic phenotype in culture cells (primary, secondary, cell lines, or explants). Cell culture assays measure the ability of a matrix to cause one or more features indicative of differentiation along an osteoblastic or chondrocytic lineage. The feature(s) can be an expression of a marker characteristic of differentiation along an osteoblastic or chondrocytic lineage, e.g. a marker that is normally expressed by osteoblast precursors, osteoblasts, chondrocytes, or precursors of chondrocytes. One suitable marker is alkaline phosphatase. Reference is made to U.S. patent application Ser. No. 11/683,938, herein incorporated by reference, for discussion of alternative in vitro assay methods.

In studies, a typical amount of DBM for implantation is 20 mg in a mouse and 40 mg in a rat. Significant increases in the growth factor dose, for example, 150× dose (or 150 times the growth factor found in normal DBM), lead to significantly more and potentially faster bone growth with larger volume bone growth, more dense bone growth, larger nodules of bone growth, higher x-ray density, and, generally, a higher osteoinductive score. Associated with this increase in osteoinductivity can be a cortical shell surrounding the nodule and some level of vascularization in the nodule. However, the ability to quantitatively measure is generally limited by the method used, and generally measured increases in osteoinductive activity are not linear with the increase in dosage. Thus, if 20 mg of DBM gives an osteoinductive activity of 1, 100 times the growth factor dose (2000 mg of DBM growth factors) does not give an osteoinductive activity of 100. Instead, it may result in an osteoinductive activity of about 20. A limitation of measurement using osteoinductive scores is that, in some situations, the system's ability to respond may be saturated. Thus, for example, if the score ranges only from 1 to 4, two samples may have the same score (4) but may not, in fact, be comparable. This is particularly the case when the bone resulting from one method or implant is qualitatively better than the bone resulting from another method or implant. That is, both methods or implants may result in an osteoinductive score of 4 but one may result in qualitatively better bone than the other. Thus, in some situations it may be desirable to test speed of growth, density, presence of cortical bone, shelling, and/or other factors showing an increase over normal demineralized bone matrix. Further, in addition to, or in lieu of, testing at 28 days, it may be desirable to test inductivity at 21 days Generally, inductivity may be measured histomorphometrically by methods known in art.

Further, delivering 100 times the growth factor dose may be challenging. In filling a bone defect, only as much filler may be used as there is bone void space.

XIII. Examples

The examples may refer to particles, particles formed into a putty, particles formed into a gel, or other. It is to be understood that the examples are illustrative only and are not intended to be limiting. Thus, each example may be modified to provide compositions having differing consistencies such as flowable, injectable, rubbery, flexible, stiff, or other.

Example 1

Surface Demineralized Heat Treated Particles

In one example, bone was cleaned of soft tissue and ground to powder ranging from 2.8 mm to 4 mm. The particles were extracted with 1:1 chloroform-methanol for 6 hours. The solvent was then decanted and the excess allowed to evaporate under a fume hood overnight. The particles were then vacuum dried overnight.

The particles were surface demineralized for 75 minutes in 0.6 N HCl and then washed with distilled water until the pH of the wash exceeded 3.0. The resulting surface demineralized particles were then incubated with agitation in 100 mM phosphate buffer, pH 7.4, containing 6.0 mM NEM and 2.0 mM sodium azide for 72 hours at 37° C.

The resulting particles were washed two times for 15 minutes in water at room temperature. The particles were lyophilized and implanted in a sheep femoral defect; the results were examined by micro-CT analysis 4 weeks and 13 weeks post-implantation.

Figure 5:
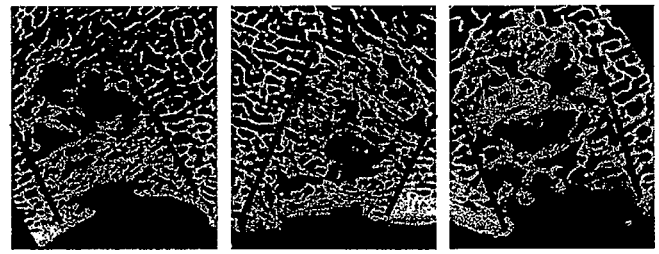
FIG. 5 comparatively illustrates site response of autograft implants versus site response of surface demineralized heat treated particle implants.
Figure 5:
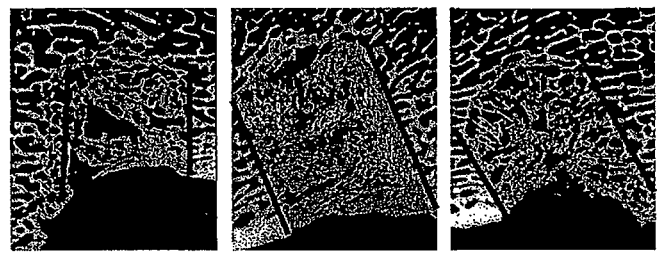

FIG. 5 illustrates the 13 week results of autograft and of surface demineralized heat treated particles.

Example 2

Surface Demineralized Heat Treated Particles

The particles are prepared as described in Example 1 excepting incubation in phosphate buffer.

Example 3a

Smaller Surface Demineralized Heat Treated Particles

Particles were ground to a size ranging from 1 mm to 2.8 mm and demineralized in 0.6N HCl for 60 minutes prior to heat treatment as described in Example 1.

Example 3b

Smaller Surface Demineralized Heat Treated Particles

Particles were ground to a size ranging from 0.5 mm to 1.0 mm and demineralized in 0.6N HCl for 10 minutes prior to heat treatment as described in Example 1.

Example 3c

Smaller Surface Demineralized Heat Treated Particles

Particles were ground to a size ranging from 0.1 mm to 0.5 mm and demineralized in 0.6N HCl for 7 minutes prior to heat treatment as described in Example 1.

Example 4a

Various Degrees of Demineralization

Particles are ground to a size ranging from 1.0 mm to 2.8 mm and demineralized for 15 minutes prior to heat treatment as described in Example 1.

Example 4b

Various Degrees of Demineralization

Particles are ground to a size ranging from 1.0 mm to 2.8 mm and demineralized for 30 minutes prior to heat treatment as described in Example 1.

Example 4c

Various Degrees of Demineralization

Particles are ground to a size ranging from 1.0 mm to 2.8 mm and demineralized for 120 minutes prior to heat treatment as described in Example 1.

Example 4d

Various Degrees of Demineralization

Particles are ground to a size ranging from 1.0 mm to 2.8 mm and demineralized for 240 minutes prior to heat treatment as described in Example 1.

Example 4e

Various Degrees of Demineralization

Particles are ground to a size ranging from 1.0 mm to 2.8 mm and demineralized for 480 minutes prior to heat treatment as described in Example 1.

Example 4f

Various Degrees of Demineralization

Particles are ground to a size ranging from 1.0 mm to 2.8 mm and fully demineralized prior to heat treatment as described in Example 1.

Example 4g

Various Degrees of Demineralization

Particles are ground to a size ranging from 2.8 mm to 4.0 mm and demineralized for 15 minutes prior to heat treatment as described in Example 1.

Example 4h

Various Degrees of Demineralization

Particles are ground to a size ranging from 2.8 mm to 4.0 mm and demineralized for 240 minutes prior to heat treatment as described in Example 1.

Example 4i

Various Degrees of Demineralization

Particles are ground to a size ranging from 2.8 mm to 4.0 mm and demineralized for 480 minutes prior to heat treatment as described in Example 1.

Example 4j

Various Degrees of Demineralization

Particles are ground to a size ranging from 2.8 mm to 4.0 mm and fully demineralized prior to heat treatment as described in Example 1.

Example 4k

Various Degrees of Demineralization

Particles are treated as described in Example 1 and above excepting incubation in phosphate buffer.

Example 5a

Mixing of Surface Demineralized Particles with DBM Fiber

Particles are made as in Example 1 and mixed with demineralized bone fibers in a ratio of 3 volumes of surface demineralized particles to 1 volume of DBM fiber.

Example 5b

Mixing of Surface Demineralized Particles with DBM Fiber

Particles are made as in Example 1 and mixed with demineralized bone fibers in a ratio of 1 volume of surface demineralized particles to 1 volume of DBM fiber.

Example 5c

Mixing of Surface Demineralized Particles with DBM Fiber

Particles are made as in Example 1 and mixed with demineralized bone fibers in a ratio of 2 volume of surface demineralized particles to 1 volume of DBM fiber.

Example 6a

Combining Surface Demineralized Heat Treated Particles with DBM Extracts

Particles made as in Example 1 are mixed with protein extracted from an equal volume of demineralized bone matrix with 4 M Guanidine HCl. The extracted proteins are added to the surface demineralized particles and the suspension is dialyzed against water until the guanidine is effectively removed. The preparation is then lyophilized.

Example 6b

Combining Surface Demineralized Heat Treated Particles with DBM Extracts

Particles made as in Example 1 are mixed with protein extracted from twice the volume of demineralized bone matrix with 4 M Guanidine HCl. The extracted proteins are added to the surface demineralized particles and the suspension is dialyzed against water until the guanidine is effectively removed. The preparation is then lyophilized.

Example 6c

Combining Surface Demineralized Heat Treated Particles with DBM Extracts

Particles made as in Example 1 are mixed with protein extracted from five times the volume of demineralized bone matrix with 4 M Guanidine HCl. The extracted proteins are added to the surface demineralized particles and the suspension is dialyzed against water until the guanidine is effectively removed. The preparation is then lyophilized.

Example 6d

Combining Surface Demineralized Heat Treated Particles with DBM Extracts

Particles made as in Example 1 are mixed with protein extracted from ten times the volume of demineralized bone matrix with 4 M Guanidine HCl. The extracted proteins are added to the surface demineralized particles and the suspension is dialyzed against water until the guanidine is effectively removed. The preparation is then lyophilized.

Example 7

Organic Precipitation of Proteins

Materials are prepared as in Example 6 excepting precipitation of proteins onto surface demineralized bone with a volume of 1:1 acetone/ethanol equal to the volume of guanidine HCl.

Example 8

Combining Surface Demineralized Heat Treated Particles with Demineralized Bone Fibers and Protein Extracts Mixtures of surface demineralized particles and demineralized bone matrix fibers described in Example 5 are combined with extracts as described in Examples 6 and 7.

Example 9

Combining Surface Demineralized Heat Treated Particles with a Carrier

Compositions as prepared by any of Examples 1-8 are combined with glycerol.

Example 9b

Combining Surface Demineralized Heat Treated Particles with a Carrier

Compositions as prepared by any of Examples 1-8 are combined with a polylactide polymer.

Example 9c

Combining Surface Demineralized Heat Treated Particles with a Carrier

Compositions as prepared by any of Examples 1-8 are combined with a polyglycolide polymer.

Example 9d

Combining Surface Demineralized Heat Treated Particles with a Carrier

Compositions as prepared by any of Examples 1-8 are combined with a polylactide-co-glycolide copolymer.

Example 9e

Combining Surface Demineralized Heat Treated Particles with a Carrier

Compositions as prepared by any of Examples 1-8 are combined with a starch.

Example 9f

Combining Surface Demineralized Heat Treated Particles with a Carrier

Compositions as prepared by any of Examples 1-8 are combined with an alginate.

Example 9g

Combining Surface Demineralized Heat Treated Particles with a Carrier

Compositions as prepared by any of Examples 1-8 are combined with chitosan.

Example 9h

Combining Surface Demineralized Heat Treated Particles with a Carrier

Compositions as prepared by any of Examples 1-8 are combined with a pluronic.

Example 9i

Combining Surface Demineralized Heat Treated Particles with a Carrier

Compositions as prepared by any of Examples 1-8 are combined with hyaluronic acid.

Example 10

Sheep cortical bone is processed to different components: 1-2.8 mm surface demineralized particles, DBM fibers and DBM powder (106-500 μm). DBM powder is extracted with 4M guanidine HCl. The guanidine hydrochloride extract is dialyzed against water and the supernatant and precipitate are separated via centrifugation. The collagenous supernatant is lyophilized to obtain dry collagen residue. 10 grams of dry surface demineralized bone are combined with 3.85 grams of dry DBM fiber and 0.85 grams dry collagen residue. The material is mixed in the presence of 20 ml water. The final mixture is injected into a mold, lyophilized to form a matrix.

Example 11

Composition is formed as in Example 10 but omitting the centrifugation of the extract and separation of supernatant from precipitate.

Example 12

Composition is formed as in Example 10 excepting that mixing in the final step is carried out in a solution of glycerol and water in a volume ratio of 45:55.

Example 13

Sheep cortical bone is processed to different components: 1-2.8 mm surface demineralized particles and DBM fibers. 10 grams of dry surface demineralized bone are combined with 3.85 grams of dry DBM fiber and 0.15 grams of chitosan. Prior to mixing the chitosan is dissolved in 5 ml of 2% acetic acid. The materials are mixed in the presence of 15 ml water. The final mixture is injected into a mold, lyophilized to form a matrix. The matrix is then treated with 5% sodium citrate for 1 hour, washed and lyophilized.

Example 14

Composition is prepared as in example 13 excepting the use of 15 ml 45:55 glycerol-water in place of 15 ml water and excluding treatment with sodium citrate.

Example 15

Sheep cortical bone is processed to different components: 1-2.8 mm surface demineralized particles and DBM powder (106-500 μm). DBM powder is extracted with 4M guanidine HCl. The guanidine hydrochloride extract is dialyzed against water and the supernatant and precipitate are separated via centrifugation. The collagenous supernatant is lyophilized to obtain dry collagen residue. 10 g surface demineralized particles are wetted in 40 ml DI water and then pressed at 4000 psi. Pressed surface demineralized particles are soaked in a mixture of glycerol/water (45/55) for 1 hour and then filtered to get around 23 grams of glycerated material. The glycerated surface demineralized particles are further combined with 1.1 grams of collagen residue in 5 ml water. The final mixture is injected into a mold and lyophilized to obtain a matrix.

Example 16

Composition prepared as in Example 14 but omitting the centrifugation step and separation of supernatant from precipitate.

Example 17

Sheep cortical bone is processed to different components: 1-2.8 mm surface demineralized particles and DBM fibers. 10 grams of dry surface demineralized bone are combined with 3.85 grams of dry DBM fiber and 0.10 grams of human or bovine derived antelocollagen. Prior to mixing the collagen is suspended in 10 ml of 2% lactic acid. The materials are mixed in the presence of 10 ml water. The final mixture is injected into a mold, lyophilized to form a matrix.

Example 18

Sheep cortical bone is processed to different components: 1-2.8 mm surface demineralized particles and DBM fibers. 10 grams of dry surface demineralized bone are combined with 3.85 grams of dry DBM fiber and 0.50 grams of polymer. Polymers can be naturally derived or synthetic such as alginate, cellulose, gelatin, poly(lactic acid), poly(lactic-co-glycolic acid), poly(caprolactone), poly(lactide-co-caprolactone), poly(carbonate), Pluronic F127 etc. Prior to mixing the polymers are dissolved in a biocompatible solvent. The components are mixed and injected into a mold, lyophilized to form a matrix.

Example 19

Sheep cortical bone is processed to different components: 1-2.8 mm surface demineralized particles, DBM fibers and DBM powder (106-500 μm). DBM powder is extracted with 4M guanidine HCl. The guanidine hydrochloride extract is dialyzed against water and the supernatant and precipitate are separated via centrifugation. The collagenous supernatant is lyophilized to obtain dry collagen residue. 10 grams of dry surface demineralized bone are combined with 3.85 grams of dry DBM fiber and 0.85 grams dry collagen residue. The material is mixed in the presence of 20 ml of water and loaded into a syringe. Any excess water is extruded.

Example 20

Composition is prepared as in example 19 but omitting the centrifugation of the extract and separation of supernatant from precipitate.

Example 21

Composition is prepared as in Example 19 excepting that mixing in the final step is carried out in a solution of glycerol and water in a volume ratio of 45:55.

Example 22

Sheep cortical bone is processed to different components: 1-2.8 mm surface demineralized particles and DBM fibers. 10 grams of dry surface demineralized bone are combined with 3.85 grams of dry DBM fiber and 0.15 grams of chitosan. Prior to mixing the chitosan is dissolved in 5 ml of 2% acetic acid. The materials are mixed in the presence of 15 ml water. The material is loaded into a syringe to obtain an extrudable formulation.

Example 23

Composition is prepared as in Example 22 excepting the use of 15 ml 45:55 glycerol-water in place of 15 ml water.

Example 24

Sheep cortical bone is processed to different components: 1-2.8 mm surface demineralized particles, DBM fibers. 10 grams of dry surface demineralized bone are combined with 3.85 grams of dry DBM fiber and 8.3 grams of hydrated starch. The material is loaded into a syringe to obtain an extrudable formulation.

Example 25

Sheep cortical bone is processed to different components: 1-2.8 mm surface demineralized particles and DBM fibers. 10 grams of dry surface demineralized bone are combined with 3.85 grams of dry DBM fiber and 0.10 grams of human or bovine derived predominantly type I collagen. Prior to mixing the collagen is suspended in 10 ml of 2% lactic acid. The materials are mixed in the presence of 10 ml water. The material is loaded into a syringe to obtain an extrudable formulation.

XIV. Assessment of Bone Particles

It may be useful to assess characteristics of the bone particles at times before, during, or after the methods provided herein.

Assessment of Neutral Protease Activity

It may be useful to assess endogenous protease activity in the bone particles. For example, in the method shown in FIG. 2, the neutral protease activity of mineralized bone is high but is reduced upon demineralization. Accordingly, the surface of the particles after demineralization has a lower protease activity than prior to demineralization. The lower protease activity allows maintenance of osteoinductive activity at the particle surface. Any suitable method of assessing protease activity may be used.

In one embodiment, the following procedure was used to assess endogenous protease activity of the bone particles. A Pierce QuantiCleave Protease Activity Kit was used. In the embodiment herein described, a modified casein substrate was used. The kit identifies exposed N-terminal amines of peptides released from the casein precursor.

All samples were processed using sterile technique. Microfuge tubes and pipette tips were autoclaved.

Generation of Finely Powdered Sterile DBM and Nondemineralized Bone

A. 1 gram of human DBM was prepared and finely powdered in a Spec Freezer Mill using the following protocol:
5 min pre-cool in LN2. (T3)
3×2 min cycles (T1)
1 min interim cooling. (T2)

B. 1 gram of powdered nondemineralized bone (mixed batches), cleaned and sonicated in ethanol, was treated as above.

Preparation of Assay Solution

PBS was used as the Assay Buffer instead of 50 mM Borate Buffer. This comprised adding 5 ml of PBS to 3 vials (10 mg) of Succinylated casein, letting stand for 5 min and gently swirling to dissolve the protein. The contents of three vials were sterile filtered into a single 15 ml SterileTube. This is known as the sterile succinylated casein solution. The volume of the sterile succinylated casein solution was adjusted to 15 ml using sterile PBS.

300 µl of succinylated casein solution was added to each of five tubes from each group.

As blanks, 300 µl of phosphate buffered saline, pH 7.4, containing 0.9 mM $CaCl_2$, 0.2 $H_2O$ and 0.5 mM $MgCl_2$ was added to five tubes from each group.

All tubes were vortexed for 20 seconds and then placed on ice for 15 minutes. The tubes were centrifuged at 12,000 rpm for 5 minutes and the vortexing and centrifugation steps were repeated.

Protease Assay

TPCK trypsin stock solution was prepared by adding 5 mg TPCK trypsin (included with Kit) to 2.5 ml of PBS. The solution was sterile filtered into a sterile 15 ml tube and the volume was raised to 10 ml.

The stock solution was serially diluted in a sterile hood by adding 1 ml of stock to 9 mo of PBS, vortexing, and continuing the 10 fold dilution series for a total of 9 standards ranging from $5.0 \times 10^{-1}$ mg/ml to $5.0 \times 10^{-9}$ mg/ml.

All samples received an additional 200 ul Casein/or 200 ul PBS.

The Standards 100 ml of succinylated casein solution was added to each of 21 sterile microfuge tubes.

The following tubes were prepared and processed as described:

| | | |
|---|---|---|
| 1. | 0.0 ng/ml trypsin | To three of the tubes add 50 ul of sterile PBS. |
| 2. | 0.005 ng/ml trypsin | To three of the tubes add 50 ul $5.0 \times 10^{-9}$ mg/ml trypsin |
| 3. | 0.05 ng/ml trypsin | To three of the tubes add 50 ul $5.0 \times 10^{-8}$ mg/ml trypsin. |
| 4. | 0.5 ng/ml trypsin | To three of the tubes add 50 ul $5.0 \times 10^{-7}$ mg/ml trypsin. |
| 5. | 5.0 ng/ml trypsin | To three of the tubes add 50 ul $5.0 \times 10^{-6}$ mg/ml trypsin. |
| 6. | 50.0 ng/ml trypsin | To three of the tubes add 50 ul $5.0 \times 10^{-5}$ mg/ml trypsin |
| 7. | 500.0 ng/ml trypsin | To three of the tubes add 50 ul $5.0 \times 10^{-4}$ mg/ml trypsin |
| 8. | 5000 ng/ml trypsin | To three of the tubes add 50 ul $5.0 \times 10^{-3}$ mg/ml trypsin |
| 9. | 50,000 ng/ml trypsin | To three of the tubes add 50 ul $5.0 \times 10^{-2}$ mg/ml trypsin |
| 10. | 500,000 ng/ml trypsin | To three of the tubes add 50 ul $5.0 \times 10^{-1}$ mg/ml trypsin |

1-9—Received 9 mls PBS
10—Received 10 mls of PBS

For each standard or sample, the following was done.

Process repeated using sterile PBS in place of succinylated casein. These tubes served as blanks for the standards.

Incubated for 24 hrs at 40° C. in a shaking water bath.

Color Development

At the end of the 120 hrs period, samples were vortexed and centrifuged at 13,000 rpm for 10 min. 150 µl of supernatant was removed from each sample and transferred to a 96 well ELISA plate.

TNBSA working solution was prepared by adding 100 ul of stock TNBSA solution to 14.9 ml PBS.

In well A1 place 200 µl of water was placed as the path length plate blank.

50 µl of TNBSA working solution was added to all other wells.

Incubated for 20 min at room temperature.

Measured absorbance at 405 nm.

Subtracted the average absorbance of each sample group from the corresponding blank.

Assessment of Depth of Demineralization

It may further be useful to assess the depth of demineralization of surface demineralized particles. Any suitable method, including measurement by x-ray, by contact x-ray, by contact microradiograph, by stain, by embedding in polymer, be microscopic study, or other may be used.

In one method, the bone particle is placed in 3% basic fuchsin in order to stain the demineralized surface. The bone particle is photographed, acquired with Adobe Photoshop 5.0, and analyzed with Image-Pro Plus 3.1. The actual depth of demineralization is calculated by measuring the length (pixels) of the stained demineralized area at several locations ($D_p$ and $D_r$) for each time point. The pixel measurements are averaged and converted to millimeters.

XV. Uses

Therapeutic Uses

The osteoinductive composition or osteoimplant is intended to be applied at a bone repair site, for example, a site resulting from injury, defect brought about during the course of surgery, infection, malignancy, or developmental malformation. The osteoinductive composition may be used for treatment of metabolic bone disease, bone healing, cartilage repair, spinal disc repair, tendon repair, repair of a defect created by disease or surgery, dural repair and may be further used in a wide variety of orthopedic, periodontal, neurosurgical, and oral and maxillofacial surgical procedures. The osteoinductive composition or osteoimplant may further be used in veterinary applications.

At the time just prior to when the osteoinductive composition or osteoimplant is to be placed in a defect site, optional materials, e.g., autograft bone marrow aspirate, autograft bone, preparations of selected autograft cells, autograft cells containing genes encoding bone promoting action, etc., can be combined with the osteoimplant. The osteoimplant can be implanted at the bone repair site, if desired, using any suitable affixation means, e.g., sutures, staples, bioadhesives, screws, pins, rivets, other fasteners and the like or it may be retained in place by the closing of the soft tissues around it.

The osteoinductive compositions may also be used as drug delivery devices. In certain embodiments, association with the osteoinductive compositions increases the half-life of the relevant biologically active agent(s). In some embodiments, the drug delivery devices may be used to deliver osteoinductive growth factors. Other preferred agents to be delivered include factors or agents that promote wound healing. However, the osteoinductive compositions may alternatively or additionally be used to deliver other pharmaceutical agents including antibiotics, anti-neoplastic agents, growth factors, hematopoietic factors, nutrients, an other bioactive agents described above. The amount of the bioactive agent included with the DBM composition can vary widely and will depend on such factors as the agent being delivered, the site of administration, and the patient's physiological condition. The optimum levels is determined in a specific case based upon the intended use of the implant.

Non-Therapeutic Uses

In addition to therapeutic uses involving implantation into a subject, the osteoinductive composition has a number of other uses. For example, it can be used to generate or culture cell lines, tissues, or organs having osteogenic or chondrogenic properties. In particular, cells can be removed from a donor and cultured in the presence of an osteoinductive composition. The invention includes such cells as well as tissues and organs derived therefrom. The cells, tissues, or organs may be implanted into the original donor after a period of culture in vitro or may be implanted into a different subject.

XVI. Conclusion

In certain embodiments, the osteoinductive compositions and associated osteoimplants produce bone or cartilage in an animal model and/or in human patients with similar timing and at a level at least 10%, 20%, 35%, 50%, 100%, 200%, 300%, or 400% or greater osteogenic, osteoinductive or chondrogenic activity than a corollary carrier that has not been exposed to a treatment or condition as described herein. One skilled in the art will appreciate that these values may vary depending on the type of test used to measure the osteoinductivity or osteogenic or chondrogenic activity described above. The test results may fall within the range of 10% to 35%, 35% to 50%, 50% to 100%, 100% to 200%, and 200% to 400%. In certain embodiments, when an osteoimplant is implanted into a bone defect site, the osteoimplant has an osteoinductivity score of at least 1, 2, 3, or 4 in an animal model and/or in humans.

Although the invention has been described with reference to specific embodiments, persons skilled in the art will recognize that changes may be made in form and detail without departing from the spirit and scope of the invention.

The invention claimed is:

1. An osteoinductive composition, the composition comprising:
   heat and gaseous supercritical carbon dioxide treated surface demineralized bone particles, the bone particles ranging from approximately 1 mm to approximately 4 mm in their longest dimension, and being approximately 10 to approximately 50% demineralized;
   demineralized bone matrix; and
   a delivery vehicle.

2. The osteoinductive composition of claim 1, wherein the surface demineralized bone particles comprise surface demineralized allograft bone particles.

3. The osteoinductive composition of claim 1, wherein the surface demineralized bone particles comprise surface demineralized xenograft bone particles.

4. The osteoinductive composition of claim 1, wherein the bone particles are approximately 10% demineralized.

5. The osteoinductive composition of claim 1, wherein the partially demineralized bone particles have a collagen structure and wherein the collagen structure of the bone has been disrupted.

6. The osteoinductive composition of claim 1, wherein the partially demineralized bone particles have been treated with atmospheric supercritical carbon dioxide at a temperature between approximately 100° C. and 250° C.

7. The osteoinductive composition of claim 1, wherein the osteoinductive composition comprises a slurry, putty, or gel.

8. The osteoinductive composition of claim 1, wherein the demineralized bone matrix comprises demineralized bone fibers.

9. The composition of claim 8, wherein the demineralized bone fibers have a median length to median thickness ratio of at least about 10:1 and up to about 500:1, a median length of from about 2 mm to about 400 mm, a medium width of from about 2 mm to about 5 mm, and a median thickness of from about 0.02 to about 2 mm.

10. The composition of claim 8, wherein the demineralized bone fibers comprise pressed demineralized bone fibers.

11. The osteoinductive composition of claim 1, wherein the delivery vehicle is a carrier.

12. The osteoinductive composition of claim 11, wherein the carrier is glycerol and wherein the osteoinductive composition is moldable.

13. The osteoinductive composition of claim 11, wherein the carrier is glycerol, and wherein the osteoinductive composition is extrudable.

14. The osteoinductive composition of claim 1, wherein the delivery vehicle is a covering.

15. The osteoinductive composition of claim 14, wherein the covering is a mesh.

16. The osteoinductive composition of claim 14, wherein the covering is tubular.

* * * * *